US012667368B2

(12) United States Patent
Thomas et al.

(10) Patent No.: US 12,667,368 B2
(45) Date of Patent: Jun. 30, 2026

(54) LIGATION CLIP APPLIER WITH CLIP RETAINING END EFFECTOR

(71) Applicant: Covidien LP, Mansfield, MA (US)

(72) Inventors: Justin J. Thomas, New Haven, CT (US); Roy J. Pilletere, Middletown, CT (US); Matthew A. Dinino, Newington, CT (US); Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 456 days.

(21) Appl. No.: 17/957,471

(22) Filed: Sep. 30, 2022

(65) Prior Publication Data

US 2023/0149025 A1     May 18, 2023

Related U.S. Application Data

(60) Provisional application No. 63/280,343, filed on Nov. 17, 2021.

(51) Int. Cl.
*A61B 17/128* (2006.01)
*A61B 17/00* (2006.01)

(52) U.S. Cl.
CPC ....... *A61B 17/1285* (2013.01); *A61B 2017/00473* (2013.01)

(58) Field of Classification Search
CPC .............. A61B 17/1285; A61B 17/122; A61B 2017/00473
See application file for complete search history.

(56) References Cited

U.S. PATENT DOCUMENTS

| | | | |
|---|---|---|---|
| 3,363,628 A | 1/1968 | Wood | |
| 3,638,847 A | 2/1972 | Noiles et al. | |
| 3,675,688 A | 7/1972 | Bryan et al. | |
| 3,735,762 A | 5/1973 | Bryan et al. | |
| 3,867,944 A | 2/1975 | Samuels | |
| 4,226,242 A | 10/1980 | Jarvik | |

(Continued)

FOREIGN PATENT DOCUMENTS

| | | |
|---|---|---|
| AU | 2013254887 A1 | 11/2013 |
| CA | 1163889 A | 3/1984 |

(Continued)

OTHER PUBLICATIONS

The extended European Search Report corresponding to European Application No. EP 07 25 3905.9, completed Jan. 29, 2008; mailed Feb. 7, 2008; (7 Pages).

(Continued)

*Primary Examiner* — Brooke Labranche
(74) *Attorney, Agent, or Firm* — Dymera IP, LLC

(57) ABSTRACT
A ligation clip applier includes first and second jaw members and an elongated shaft assembly secured thereto. The elongated shaft assembly includes a tube supporting clips therein and a tab assembly supported within the tube and including angled tabs engaged with the clips for moving the clips through the tube in response to movement of the tab assembly relative to the tube. The tab assembly is positionable to load a distal-most clip into the end effector when the tab assembly moves relative to the tube. The tube is selectively engageable with an outer surface of the first and second jaw members to clamp the distal-most clip between the first and second jaw members.

20 Claims, 28 Drawing Sheets

(56)  References Cited

U.S. PATENT DOCUMENTS

| | | |
|---|---|---|
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |

(56)                References Cited

U.S. PATENT DOCUMENTS

| | | | |
|---|---|---|---|
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |

(56) References Cited

U.S. PATENT DOCUMENTS

| | | | |
|---|---|---|---|
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | Mcclellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |

(56)     References Cited

U.S. PATENT DOCUMENTS

| | | | |
|---|---|---|---|
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |
| 8,821,516 B2 | 9/2014 | Huitema |
| 8,828,023 B2 | 9/2014 | Neff et al. |
| 8,839,954 B2 | 9/2014 | Disch |

(56) References Cited

U.S. PATENT DOCUMENTS

| | | | |
|---|---|---|---|
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |

(56) References Cited

U.S. PATENT DOCUMENTS

| | | |
|---|---|---|
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Larson et al. |
| 2014/0074143 A1 | 3/2014 | Fitzgerald et al. |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1* | 1/2018 | Bhatnagar ............ A61B 17/105 |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0271536 A1 | 9/2018 | Shellenberger et al. |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |

(56) References Cited

U.S. PATENT DOCUMENTS

| | | | |
|---|---|---|---|
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | | |
|---|---|---|---|
| CN | 103251441 A | 8/2013 |
| CN | 104605911 B | 2/2017 |
| DE | 202005001664 U1 | 5/2005 |
| DE | 202007003398 U1 | 6/2007 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 1769757 A1 | 4/2007 |
| EP | 3132756 A1 | 2/2017 |
| GB | 2073022 A | 10/1981 |
| JP | 2003033361 A | 2/2003 |
| JP | 2006154230 A | 6/2006 |
| JP | 2006277221 A | 10/2006 |
| JP | 2008017876 A | 1/2008 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

International Search Report corresponding to International Application No. PCT-US08-58185, completed Sep. 4, 2008; mailed Sep. 9, 2008; (2 Pages).

The International Search Report corresponding to International Application No. PCT-US08-59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

The extended European Search Report corresponding to European Application No. EP 09 25 2049.3, completed Dec. 11, 2009; mailed Jan. 12, 2010; (3 Pages).

The extended European Search Report corresponding to European Application No. EP 09 25 2050.1, completed Dec. 23, 2009; mailed Jan. 21, 2010; (3 Pages).

The extended European Search Report corresponding to European Application No. EP 09 25 2051.9, completed Dec. 21, 2009; mailed Jan. 28, 2010; (3 Pages).

The extended European Search Report corresponding to European Application No. EP 09 25 2052.7, completed Nov. 16, 2009; mailed Nov. 24, 2009; (3 Pages).

The extended European Search Report corresponding to European Application No. EP 09 25 2053.5, completed Nov. 24, 2009; mailed Dec. 1, 2009; (3 Pages).

The extended European Search Report corresponding to European Application No. EP 09 25 2054.3, completed Jan. 7, 2010; mailed Jan. 22, 2010; (3 Pages).

The extended European Search Report corresponding to European Application No. EP 09 25 2056.8, completed Jan. 8, 2010; mailed Feb. 5, 2010; (3 Pages).

The extended European Search Report corresponding to European Application No. EP 10 25 0497.4, completed May 4, 2010; mailed May 12, 2010; (6 Pages).

The extended European Search Report corresponding to European Application No. EP 10 25 2079.8, completed Mar. 8, 2011; mailed Mar. 17, 2011; (3 Pages).

The European Search Report corresponding to European Application No. EP 05 81 0218.7, completed Apr. 18, 2011; mailed May 20, 2011; (3 pages).

The European Search Report corresponding to European Application No. EP 05 80 7612.6, completed May 2, 2011; mailed May 20, 2011; (3 pages).

The extended European Search Report corresponding to European Application No. EP 10 25 1737.2, completed May 9, 2011; mailed May 20, 2011; (4 pages).

The extended European Search Report corresponding to European Application No. EP 11 25 0214.1, completed May 25, 2011; mailed Jun. 1, 2011; (3 Pages).

The extended European Search Report corresponding to European Application No. EP 11 00 2681.2, completed May 31, 2011; mailed Jun. 10, 2011; (3 Pages).

The European Search Report corresponding to European Application No. EP 05 80 2686.5, completed Jan. 9, 2012; mailed Jan. 18, 2012; (3 Pages).

The extended European Search Report corresponding to European Application No. EP 12 15 1313.9, completed Mar. 20, 2012 and mailed Apr. 12, 2012; (5 Pages).

The extended European Search Report corresponding to European Application No. EP 12 16 1291.5, completed Apr. 24, 2012 and mailed May 4, 2012; (5 Pages).

The extended European Search Report corresponding to European Application No. EP 12 16 5891.8, completed Jun. 12, 2012 and mailed Jun. 20, 2012; (6 Pages).

The extended European Search Report corresponding to European Application No. EP 12 16 2288.0, completed Jun. 4, 2012 and mailed Jul. 7, 2012; (6 Pages).

The extended European Search Report corresponding to European Application No. EP 12 16 4955.2, completed Aug. 23, 2012 and mailed Sep. 4, 2012; (5 Pages).

The extended European Search Report corresponding to European Application No. EP 11 25 0754.6, completed Oct. 22, 2012 and mailed Oct. 31, 2012; (6 Pages).

The extended European Search Report corresponding to European Application No. EP 12 18 6401.1, completed Nov. 22, 2012 and mailed Nov. 30, 2012; (7 Pages).

The extended European Search Report corresponding to European Application No. EP 12 18 6448.2, completed Nov. 28, 2012 and mailed Dec. 10, 2012; (6 Pages).

The extended European Search Report corresponding to European Application No. EP 12 19 1706.6, completed Dec. 19, 2012 and mailed Jan. 8, 2013; (6 Pages).

The Extended European Search Report corresponding to EP 12 19 8745.7, completed Mar. 19, 2013 and mailed Apr. 11, 2013; (8 Pages).

The Extended European Search Report corresponding to EP 12 15 2989.5, completed Apr. 9, 2013 and mailed Apr. 18, 2013; (9 Pages).

The Extended European Search Report corresponding to EP 08 73 2820.9, completed Jul. 2, 2013 and mailed Jul. 9, 2013; (10 Pages).

The Extended European Search Report corresponding to EP 13 17 2008.8, completed Aug. 14, 2013 and mailed Aug. 28, 2013; (8 Pages).

The Extended European Search Report corresponding to EP 13 16 6382.5, completed Nov. 19, 2013 and mailed Nov. 28, 2013; (8 Pages).

(56)            References Cited

OTHER PUBLICATIONS

The Extended European Search Report corresponding to EP 11 25 0194.5, completed Nov. 25, 2013 and mailed Dec. 3, 2013; (8 Pages).

The Extended European Search Report corresponding to EP 10 25 1798.4, completed Dec. 12, 2013 and mailed Jan. 2, 2014; (9 Pages).

"Salute II Disposable Fixation Device", Technique Guide—Laparoscopic and Open Inguinal and Ventral Hernia Repair; Davol, A Bard Company, 2006; (7 Pages).

The Extended European Search Report corresponding to EP 10 25 2112.7, completed Jul. 29, 2014 and mailed Aug. 5, 2014; (8 pp).

The Extended European Search Report corresponding to EP 14 15 1673.2, completed Apr. 25, 2014 and mailed May 8, 2014; (8 pp).

Japanese Office Action corresponding to JP 2011-160130 mailed Dec. 1, 2014.

Chinese Office Action corresponding to CN 201210015011.8 issued Jan. 4, 2015.

Japanese Office Action corresponding to JP 2011-160126 mailed Jan. 9, 2015.

Japanese Office Action corresponding to JP 2011-184521 mailed Jan. 15, 2015.

Extended European Search Report corresponding to 14 18 2236.1 dated Jan. 20, 2015.

Chinese Office Action corresponding to CN 201110201736.1 issued Feb. 9, 2015.

Extended European Search Report corresponding to EP 14 16 1540.1 dated Feb. 27, 2015.

Australian Office Action corresponding to AU 2010226985 issued Mar. 31, 2015.

Australian Office Action corresponding to AU 2013211526 issued Apr. 6, 2015.

Australian Office Action corresponding to AU 2011211463 issued Apr. 13, 2015.

Australian Office Action corresponding to AU 2013254887 issued Apr. 14, 2015.

Japanese Office Action corresponding to JP 2013-225272 mailed May 1, 2015.

Chinese First Office Action corresponding to Chinese Appln. No. CN 2014104295806 dated Aug. 31, 2017.

Extended European Search Report corresponding to European Appln. No. EP 17 17 3508.7 dated Sep. 29, 2017.

Chinese Second Office Action corresponding to Chinese Appln. No. CN 201410076318.8 dated Oct. 10, 2017.

Extended European Search Report corresponding to European Appln. No. EP 17 18 0570.8 dated Dec. 6, 2017.

Extended European Search Report corresponding to Patent Application EP 18154617.7 dated Jun. 25, 2018.

Extended European Search Report corresponding to Patent Application EP 18155158.1 dated Jun. 28, 2018.

Extended European Search Report corresponding to Patent Application EP 15877428.1 dated Jul. 2, 2018.

Extended European Search Report corresponding to Patent Application EP 18157789.1 dated Jul. 5, 2018.

Canadian Office Action corresponding to Patent Application CA 2,972,444 dated Aug. 9, 2018.

Extended European Search Report corresponding to Patent Application EP 18156458.4 dated Sep. 3, 2018.

Extended European Search Report corresponding to Patent Application EP 18171682.0 dated Sep. 18, 2018.

Extended European Search Report corresponding to Patent Application EP 15878354.8 dated Sep. 19, 2018.

Extended European Search Report corresponding to Patent Application EP 18183394.8 dated Sep. 28, 2018.

Extended European Search Report corresponding to Patent Application EP 18163041.9 dated Sep. 28, 2018.

Extended European Search Report corresponding to Patent Application EP 18170524.5 dated Oct. 1, 2018.

Japanese Office Action corresponding to Patent Application JP 2017-536546 mailed Oct. 15, 2018.

Extended European Search Report corresponding to Patent Application EP 18187640.0 dated Nov. 30, 2018.

Extended European Search Report corresponding to Patent Application EP 18187690.5 dated Nov. 30, 2018.

Chinese First Office Action corresponding to Patent Application CN 201510696298.9 dated Dec. 3, 2018.

Extended European Search Report corresponding to Patent Application EP 18158143.0 dated Dec. 5, 2018.

International Search Report corresponding to Int'l Patent Appln. PCT/US2018/050316 mailed Dec. 31, 2018.

International Search Report corresponding to Int'l Patent Appln. PCT/US2018/050336 mailed Jan. 7, 2019.

International Search Report corresponding to Int'l Patent Appln. PCT/US2018/050325 mailed Jan. 7, 2019.

International Search Report corresponding to Int'l Patent Appln. PCT/US2018/045306 mailed Jan. 16, 2019.

International Search Report corresponding to Int'l Patent Appln. PCT/US2018/050349 mailed Jan. 21, 2019.

International Search Report corresponding to Int'l Patent Appln. PCT/US2018/045725 mailed Jan. 28, 2019.

Extended European Search Report corresponding to European Patent Application EP 18208630.6 dated Feb. 12, 2019.

International Search Report corresponding to Int'l Patent Appln. PCT/US2018/057910 mailed Feb. 22, 2019.

International Search Report corresponding to Int'l Patent Appln. PCT/US2018/057922 mailed Feb. 22, 2019.

International Search Report corresponding to Int'l Patent Appln. PCT/US2018/058078 mailed Feb. 22, 2019.

International Search Report corresponding to Int'l Patent Appln. PCT/US2018/058603 mailed Feb. 22, 2019.

International Search Report corresponding to Int'l Patent Appln. PCT/US2018/057221 mailed Mar. 11, 2019.

Extended European Search Report corresponding to European Patent Application EP 18212043.6 dated Apr. 24, 2019.

Extended European Search Report corresponding to European Patent Application EP 18211565.9 dated Apr. 26, 2019.

Extended European Search Report corresponding to European Patent Application EP 18211921.4 dated Apr. 30, 2019.

Chinese First Office Action corresponding to Chinese Patent Application CN 201510868226.8 dated May 29, 2019.

Extended European Search Report corresponding to European Patent Application EP 15905685.2 dated May 29, 2019.

European Office Action corresponding to European Patent Application EP 17157606.9 dated Jul. 2, 2019.

Extended European Search Report corresponding to European Patent Application EP 15908025.8 dated Jul. 2, 2019.

Extended European Search Report corresponding to European Patent Application EP 18212054.3 dated Jul. 3, 2019.

Partial Supplementary European Search Report corresponding to European Patent Application EP 16884297.9 dated Jul. 30, 2019.

European Office Action corresponding to EP 12 152 989.5 dated May 4, 2015.

Australian Office Action corresponding to AU 2009212759 issued May 7, 2015.

Chinese Office Action corresponding to Int'l Appln No. CN 201210212642.9 dated Jun. 3, 2015.

European Office Action corresponding to Int'l Appln No. EP 04 719 757.9 dated Jun. 12, 2015.

European Office Action corresponding to Int'l Appln No. EP 13 166 382.5 dated Jun. 19, 2015.

Japanese Office Action corresponding to Int'l Application No. JP 2010-226908 dated Jun. 26, 2015.

Extended European Search Report corresponding to Int'l Application No. EP 15 15 5024.1 dated Jul. 17, 2015.

Extended European Search Report corresponding to Int'l Application No. EP 14 19 2026.4 dated Jul. 17, 2015.

Japanese Office Action corresponding to Int'l Application No. JP 2011-160126 dated Aug. 10, 2015.

Extended European Search Report corresponding to Int'l Application No. EP 14 15 0321.9 dated Sep. 23, 2015.

Extended European Search Report corresponding to Int'l Application No. EP 11 25 0675.3 dated Oct. 7, 2015.

(56)             References Cited

OTHER PUBLICATIONS

Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int'l Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.

Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 mailed Feb. 14, 2017.
European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.

* cited by examiner 25a  25b 32  33z

33p

24

24b

25c

33

33a

33y

34

25a

33b 33c  33a 32, 34

33d

33f

33x 33e  33d

33

26a

26b

24

24b

26b

24b

24a

24b

26a

60

62

62

62

LIGATION CLIP APPLIER WITH CLIP RETAINING END EFFECTOR

CROSS REFERENCE TO RELATED APPLICATIONS

This application claims the benefit of U.S. Provisional Patent Application Ser. No. 63/280,343, filed Nov. 17, 2021, the entire contents of which are hereby incorporated by reference herein.

FIELD

This disclosure is directed to ligation clip appliers for applying ligation clips to tissue and, more particularly, to multi-fire ligation clip appliers including an end effector for retaining the ligation clip within the end effector.

BACKGROUND

Ligation clip appliers for applying ligation clips to tissue are used during a variety of different types of surgical procedures to ligate body vessels. Some ligation clip appliers include clip cartridges that hold a plurality of ligation clips that can be sequentially fed to jaws of the clip applier to allow the clip applier to apply a plurality of clips onto tissue without removing the clip applier from a surgical site. These clip appliers are called multi-fire ligation clip appliers.

Multi-fire ligation clip appliers typically include an actuator handle, and elongated body, and an end effector supported on a distal end portion of the elongated body. The end effector includes first and second jaws that are movable in relation to each other between open and clamped positions. The elongated body supports a supply of ligation clips that are fed sequentially from the elongated body of the ligation clip applier into the end effector. When one of the clips is received within the end effector, the ligation clip must be properly supported between the jaws to allow application of the ligation clip to tissue. If the ligation clip is not properly supported between the jaws, the ligation clip can fall from between the jaws of the end effector or become disengaged from the jaws of the end effector such that the ligation clip cannot be properly applied to tissue.

SUMMARY

One aspect of the disclosure is directed to a ligation clip applier including an end effector and an elongated shaft assembly. The end effector includes a first jaw member and a second jaw member. The elongated shaft assembly defines a longitudinal axis and is configured to support a plurality of clips. The elongated shaft assembly is secured to the first and second jaw members. The elongated shaft assembly includes an outer tube and an inner tube supported within the outer tube. The outer tube is movable relative to the inner tube to move the first and second jaw members relative to one another. The elongated shaft assembly includes a stationary tab assembly and a movable tab assembly supported within the inner tube and configured to engage the plurality of clips. The movable tab assembly is axially movable relative to the stationary tab assembly to move the plurality of clips relative to the end effector. The movable tab assembly includes a flexible finger assembly supported on a distal end portion of the movable tab assembly and is positionable in a first position to load a first clip of the plurality of clips into the end effector when the movable tab assembly is advanced distally to a second position. The flexible finger assembly is pivotable relative to a second clip of the plurality of clips when the movable tab assembly is retracted proximally from the second position to the first position. The flexible finger assembly is configured to selectively load the second clip into the end effector when retracted back to the first position.

In aspects, the first jaw member may include a first jaw and mounting legs extending proximally from the first jaw. The mounting legs may be coupled to a jaw retainer secured to the inner tube. The first jaw may include an inner surface that defines a clip slot configured to support one clip of the plurality of clips at a time. The first jaw may include an outer surface having a proximal closing surface and a distal clamping mound that are engageable with the outer tube. The outer tube may include a distal finger that is engageable with the proximal closing surface to move the first jaw member from an open position to a closed position for supporting the one clip between the first and second jaw members in an unclamped position. The distal finger may be engageable with the distal clamping mound to move the first jaw member from the closed position to a clamping position for clamping a first leg and a second leg of the one clip together into a clamped position.

In aspects, the ligation clip applier may further include a lateral stability arm extending from the elongated shaft assembly and configured to engage a proximal end portion of the one clip.

In aspects, the movable tab assembly may include an elongated bar defining a plurality of interconnected tab sections, each tab section including a first tab that is angled inwardly toward the plurality of clips. Each tab section may further include a second tab that is angled inwardly toward the plurality of clips and a second elongated rib that is disposed between the first and second tabs.

In aspects, the ligation clip applier may further include flexible retainers secured to the first and second jaw members to facilitate securement of the first or second clips within the end effector.

Another aspect of this disclosure is directed to a surgical device including an end effector and an elongated shaft assembly. The end effector includes a first jaw member and a second jaw member. The elongated shaft assembly defines a longitudinal axis and is configured to support a plurality of clips. The elongated shaft assembly is secured to the end effector. The elongated shaft assembly includes a tube movable relative to the end effector. The elongated shaft assembly includes a movable tab assembly supported within the tube and including a plurality of tabs configured to engage the plurality of clips. The movable tab assembly is axially movable relative to the longitudinal axis to move the plurality of clips relative to the end effector. The movable tab assembly is positionable to load a first clip of the plurality of clips into the end effector when the movable tab assembly is advanced distally to a second position. The tube is engageable with the first and second jaw members to clamp the first clip between the first and second jaw members.

In aspects, the first jaw member may include a first jaw and mounting legs extending proximally from the first jaw. The mounting legs may be coupled to a jaw retainer supported within the tube. The first jaw may include an inner surface that defines a clip slot configured to support one clip of the plurality of clips at a time. The first jaw may include an outer surface having a proximal closing surface and a distal clamping mound that are engageable with the tube. The tube may include a distal finger that is engageable with the proximal closing surface to move the first jaw member from an open position to a closed position for supporting the one clip between the first and second jaw members in an unclamped position. The distal finger may be engageable with the distal clamping mound to move the first jaw member from the closed position to a clamping position for clamping a first leg and a second leg of the one clip together into a clamped position.

In aspects, the surgical device may further include a lateral stability arm extending from the elongated shaft assembly and configured to engage a proximal end portion of the one clip.

In aspects, the movable tab assembly may include an elongated bar defining a plurality of interconnected tab sections, each tab section including a plurality of tabs that is angled inwardly toward the plurality of clips.

In aspects, the surgical device may further include flexible retainers secured to the first and second jaw members to facilitate securement of the first clip within the end effector.

According to another aspect, this disclosure is directed to a surgical device including a plurality of clips, a first jaw member, a second jaw member, and an elongated shaft assembly. Each clip includes a hook and a catch configured to interlock with one another. The elongated shaft assembly is secured to the first and second jaw members and defines a longitudinal axis. The elongated shaft assembly includes a tube supporting the plurality of clips therein. The elongated shaft assembly includes a tab assembly supported within the tube and includes a plurality of angled tabs engaged with the plurality of clips for moving the plurality of clips through the tube in response to movement of the tab assembly relative to the tube. The tab assembly is positionable to load a distal-most clip of the plurality of clips into the end effector when the tab assembly moves relative to the tube. The tube is selectively engageable with an outer surface of the first and second jaw members to clamp the distal-most clip between the first and second jaw members such that the hook and the catch of the distal-most clip interlock with one another.

Other features of the disclosure will be appreciated from the following description.

BRIEF DESCRIPTION OF THE DRAWINGS

Various aspects of the disclosed ligation clip applier are described herein below with reference to the drawings, wherein.

DETAILED DESCRIPTION

Figure 1:
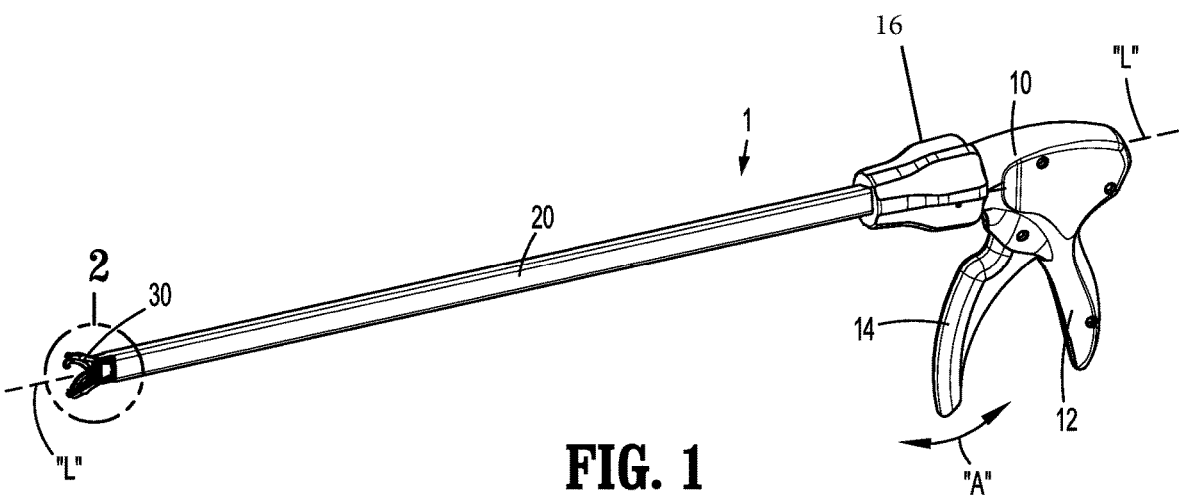
FIG. 1 is a perspective view of a ligation clip applier according to exemplary aspects of the disclosure.
Figure 2:
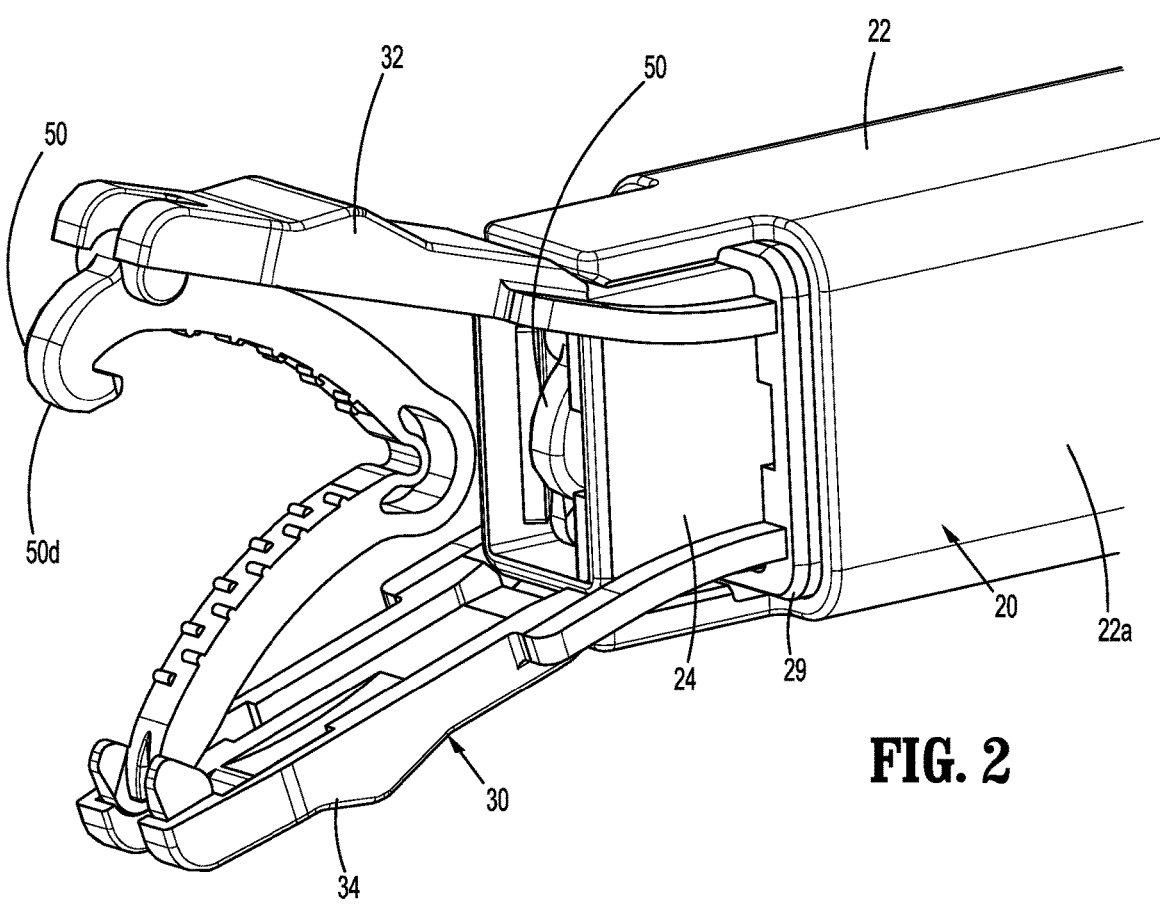
FIG. 2 is an enlarged view of the indicated area of detail shown in FIG. 1 illustrating an end effector of the ligation clip applier of FIG. 1 supporting a distal-most clip in an opened position.
Figure 3:
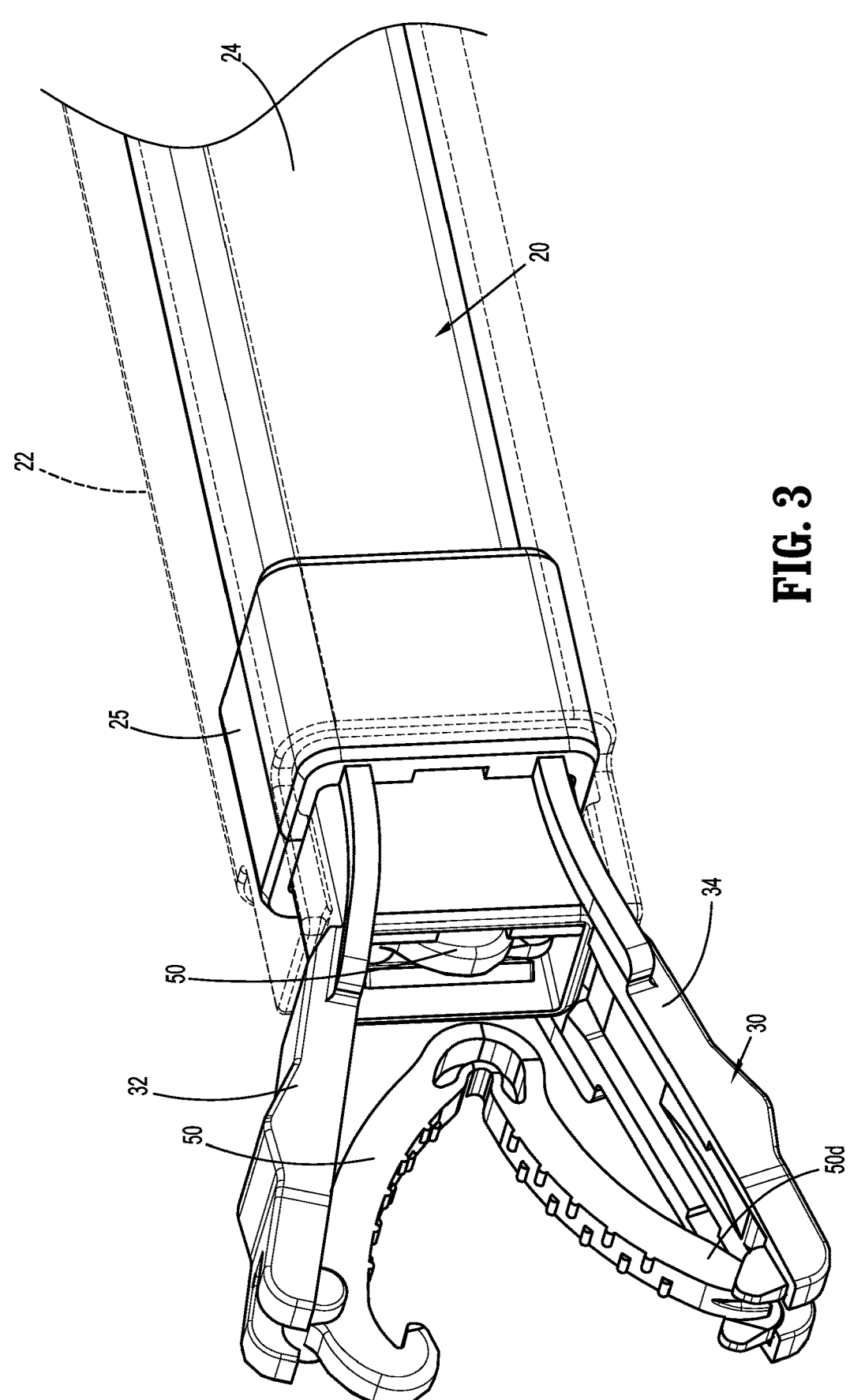
FIG. 3 is another view of FIG. 2 with portions thereof shown in phantom for clarity.
Figure 4:
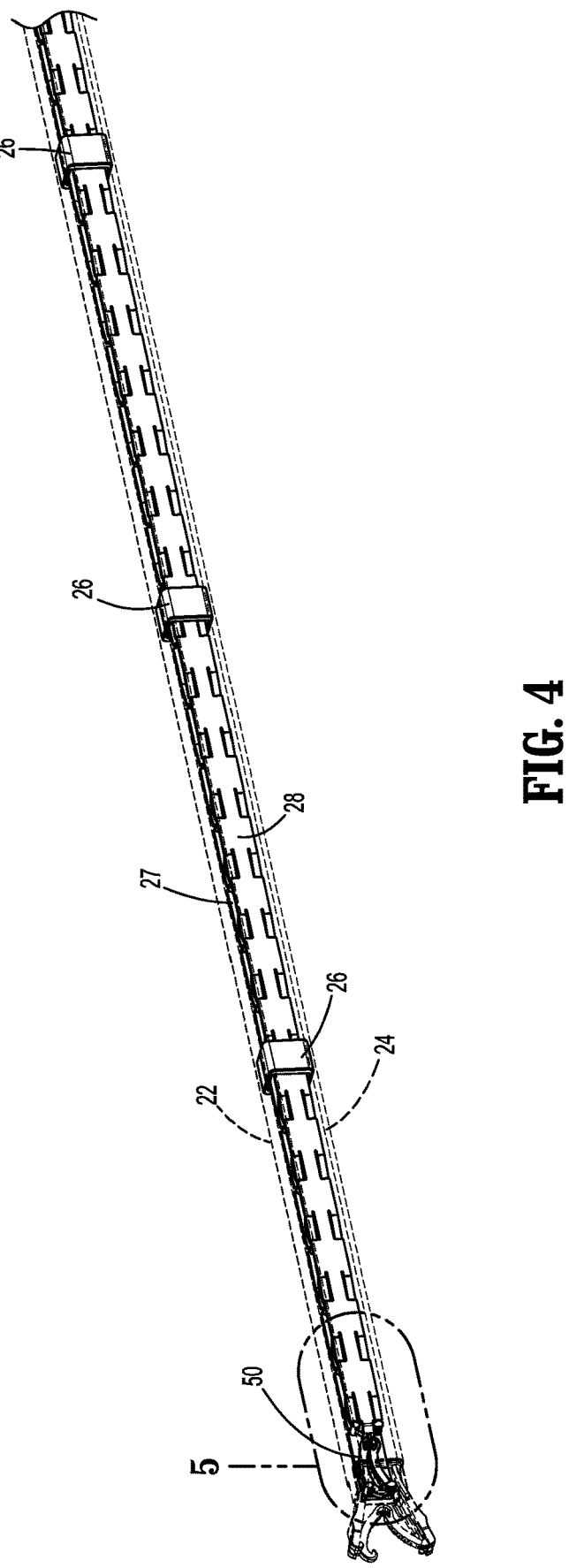
FIG. 4 is a perspective view of a distal portion of the ligation clip applier of FIG. 1 with portions removed and/or shown in phantom for clarity.
Figure 5:
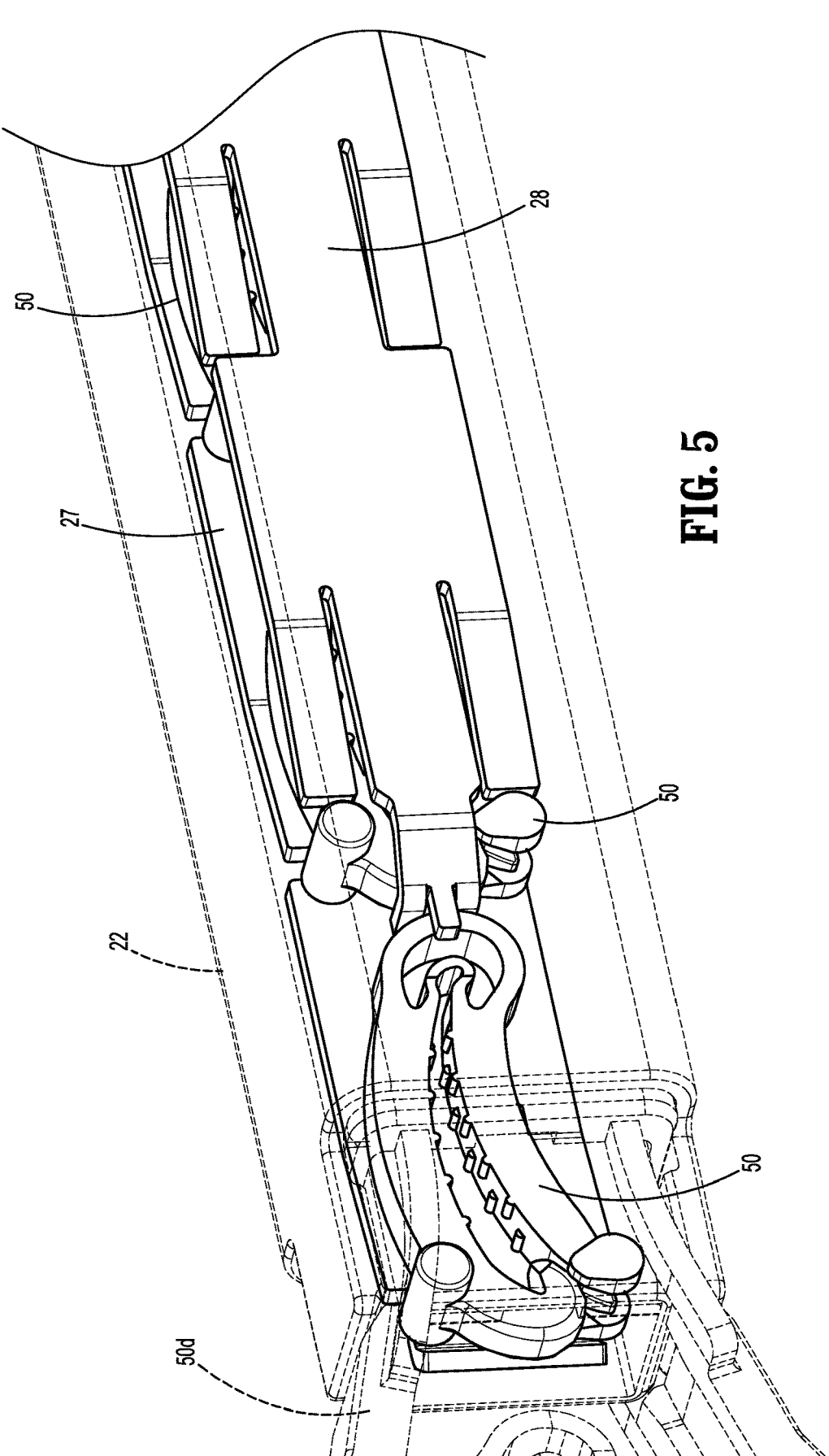
FIG. 5 is an enlarged view of the indicated area of detail shown in FIG. 4 illustrating a clip for loading into the end effector.
Figure 6:
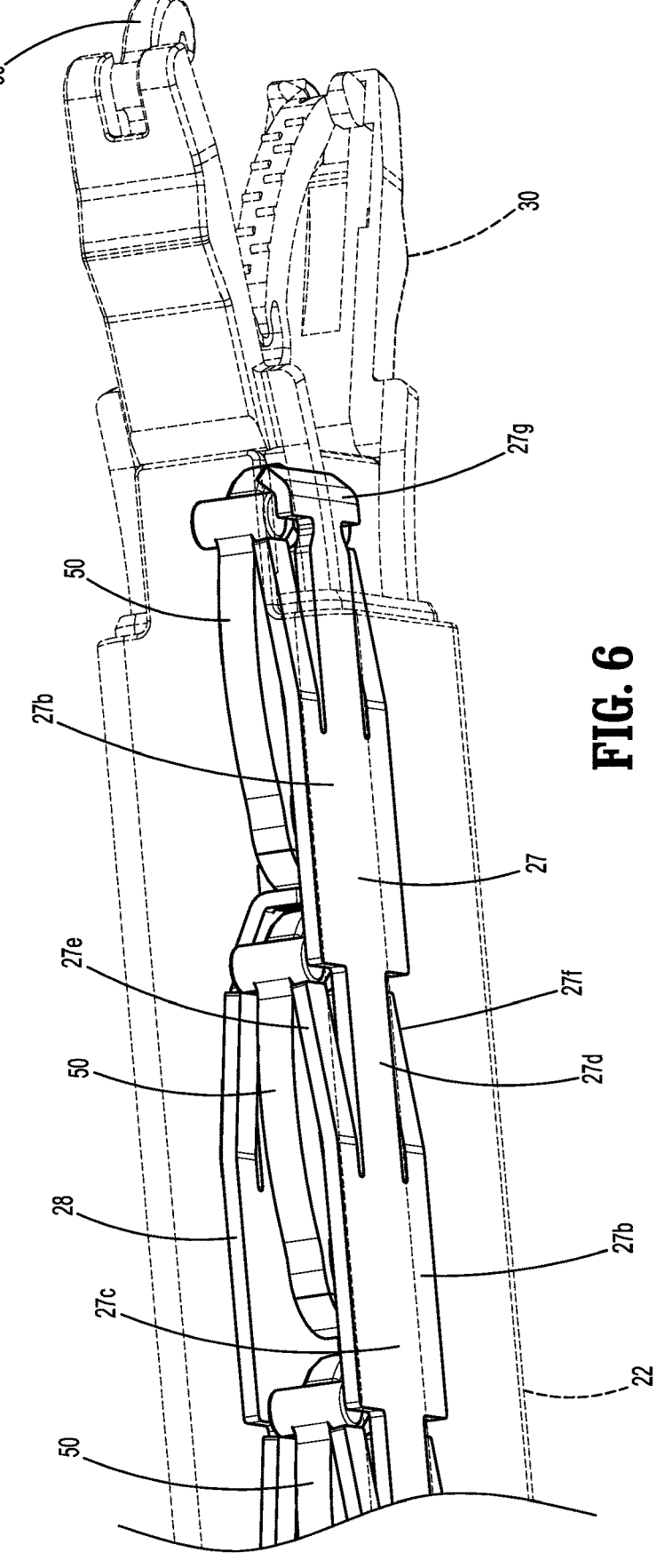
FIG. 6 is an enlarged, top, perspective view of a distal portion of the ligation clip applier of FIG. 1 with portions thereof shown in phantom for clarity.
Figure 7:
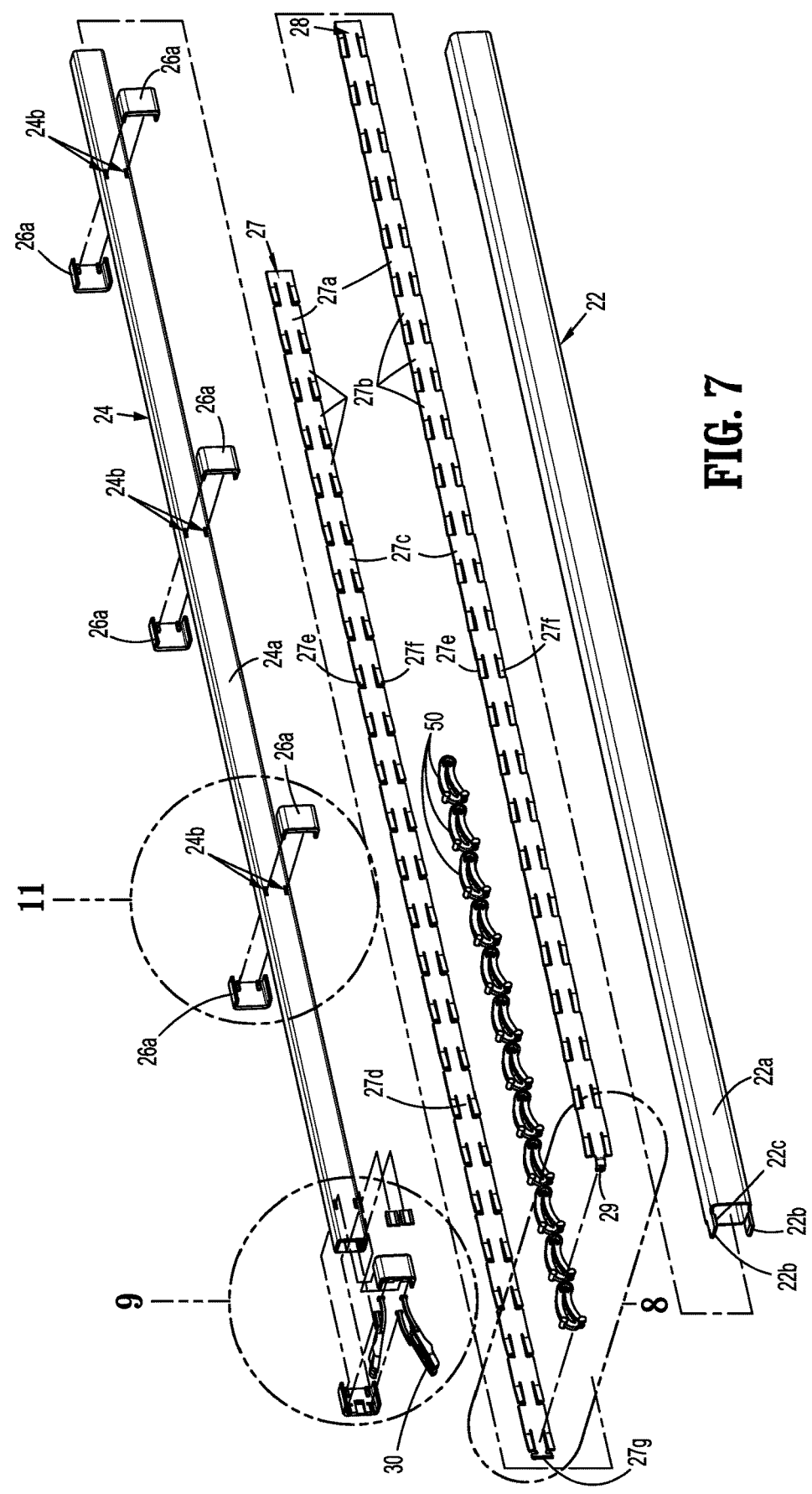
FIG. 7 is a perspective view, with parts separated, of a distal portion of the ligation clip applier of FIG. 1.
Figure 8:
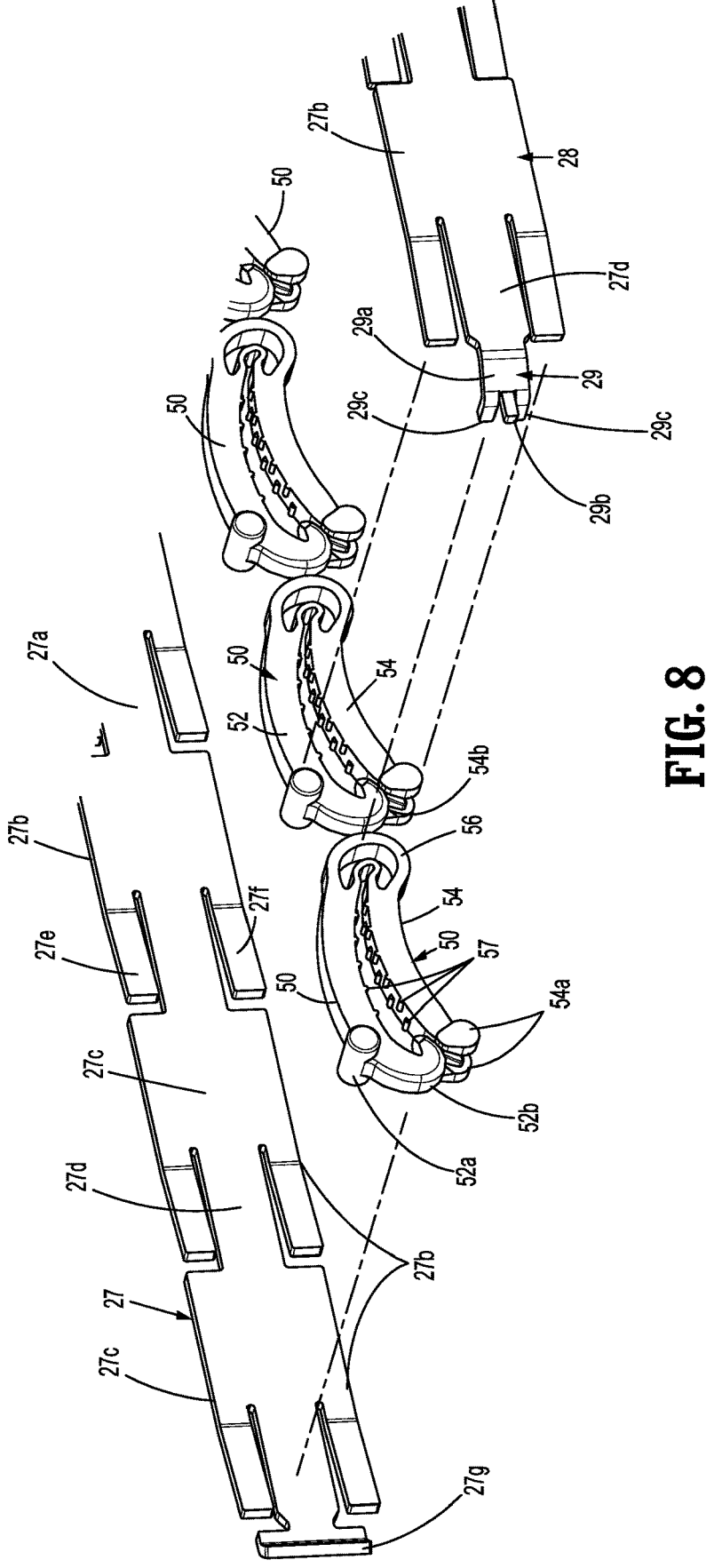
FIGS. 8, 9, and 11 are enlarged, perspective views, with parts separated, of the respective indicated areas of detail shown in FIG. 7 illustrating various components of the distal portion of the ligation clip applier of FIG. 1.

The disclosed ligation clip applier will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

With reference to FIGS. 1-25, a ligation clip applier 1 includes a handle assembly 10, an elongated shaft assembly 20 extending distally from handle assembly 10, and an end effector 30 supported on a distal end portion of elongated shaft assembly 20. Handle assembly 10 has a stationary handle 12 and one or more triggers 14 that are movable relative to stationary handle 12, as indicated by arrows "A," for actuating ligation clip applier 1. Handle assembly 10 further includes a rotatable knob 16 supported on a proximal end portion of elongated shaft assembly 20 to facilitate rotation of elongated shaft assembly 20 and end effector 30 about a longitudinal axis "L-L" defined therethrough.

End effector 30 of ligation clip applier 1 includes a first jaw member 32 and a second jaw member 34 that have proximal end portions secured to a distal end portion of elongated shaft assembly 20. First and second jaw members 32, 34 are movable between an open position (FIG. 2) and a closed position (FIG. 14) to selectively secure clips 50, one at a time, to tissue "T" (see FIGS. 23 and 25). Clips 50 are supported in elongated shaft assembly 20, in a longitudinal arrangement (e.g., tip-to-tail). Clips 50 are configured for sequential distal advancement through elongated shaft assembly 20 and into end effector 30 between first and second jaw members 32, 34 such that each clip of clips 50 becomes a distal-most clip 50*d* of clips 50 that can be fired from end effector 30 when loaded therein.

Elongated shaft assembly 20 of ligation clip applier 1 includes an outer tube 22, an inner tube 24, a jaw retainer 25, tube spacers 26 that separate outer and inner tubes 22, 24, a stationary tab assembly 27, and a movable tab assembly 28.

Outer tube 22 of elongated shaft assembly 20 has a rectangular body 22*a*, which may be any suitable shape, that extends distally to distal fingers 22*b*. Distal fingers 22*b* have teeth 22*c* (FIG. 16) that are disposed in mirrored relationship to one another and are configured to selectively engage proximal end portions of first and second jaw members 32, 34 as outer tube 22 moves relative to end effector 30.

Inner tube 24 of elongated shaft assembly 20 has a rectangular body 24*a*, which may be any suitable shape, and which is supported within outer tube 22. Rectangular body 24*a* defines spacer slots 24*b* at spaced apart locations along rectangular body 24*a*, and which may extend through both sides of rectangular body 24*a*, to facilitate securement of segments of tube spacers 26 thereto.

Figures 9, 10, 11:
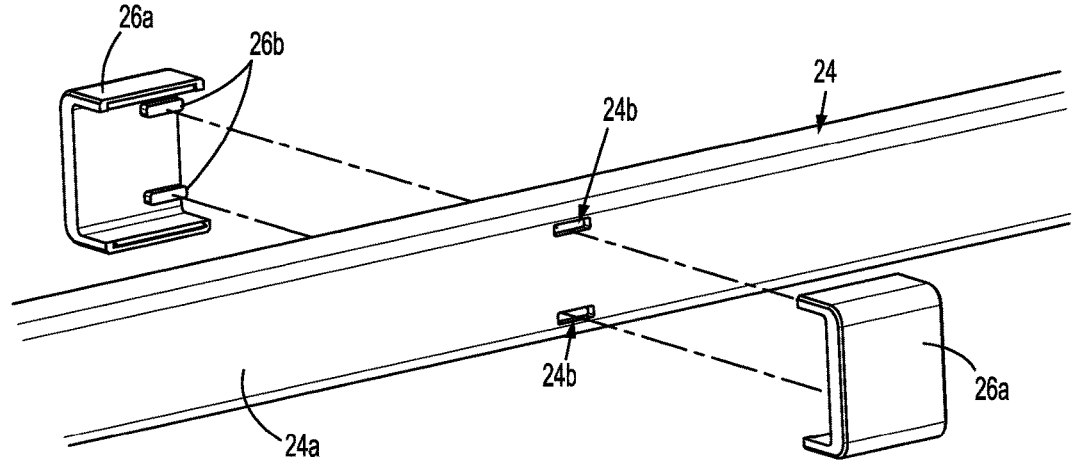
FIG. 10 is an enlarged, top, perspective view of a jaw member of the end effector of FIG. 2.
Figures 12, 13:
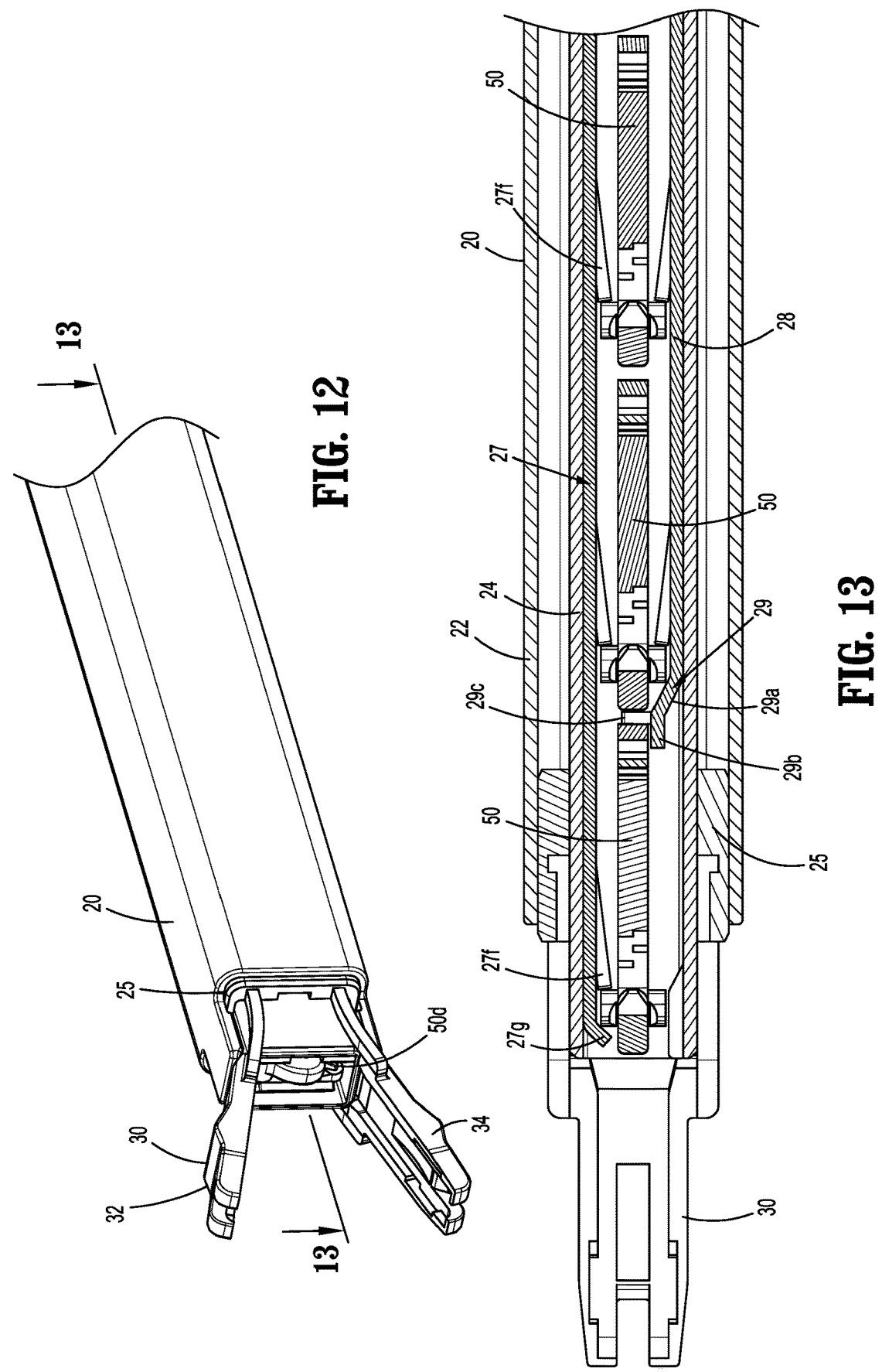
FIG. 12 is a perspective view of the distal end portion of the of the ligation clip applier of FIG. 1 with the jaw members of the end effector shown in an open position without a clip disposed therebetween.
FIG. 13 is an enlarged, cross-sectional view of FIG. 12 as taken along section line 13-13.

Tube spacers 26 of elongated shaft assembly 20 have segments 26*a*, which may be C or U-shaped, that connect together about inner tube 24. As best seen in FIG. 11, each segment 26*a* includes spaced apart prongs 26*b* extending from an inner surface thereof. Prongs 26*b* are receivable within spacer slots 24*b* of inner tube 24 to secure segments 26*a* to the respective sides of inner tube 24.

Stationary tab assembly 27 of elongated shaft assembly 20 is configured to resist movement of clips 50 in a proximal direction and includes an elongated bar 27*a* defining a plurality of interconnected tab sections 27*b*. Each tab section 27*b* includes a base 27*c* having a central elongated rib 27*d* extending distally from base 27*c* and separating first and second tabs 27*e*, 27*f* disposed on opposite sides of central elongated rib 27*d*. First and second tabs 27*e*, 27*f* are angled inwardly (e.g., at an acute angle relative to base 27*c* and central elongated rib 27*d*) toward clips 50 and movable tab assembly 28 of elongated shaft assembly 20 to assist in retaining clips 50 in position prior to loading into end effector 30. A distal most tab section 27*b* of elongated bar 27*a* includes an abutment 27*g* extending from a distal end portion of the central elongated rib 27*d* thereof. Abutment 27*g* extends transverse to central elongated rib 27*d* and curls inwardly (see FIG. 8).

Figure 17:
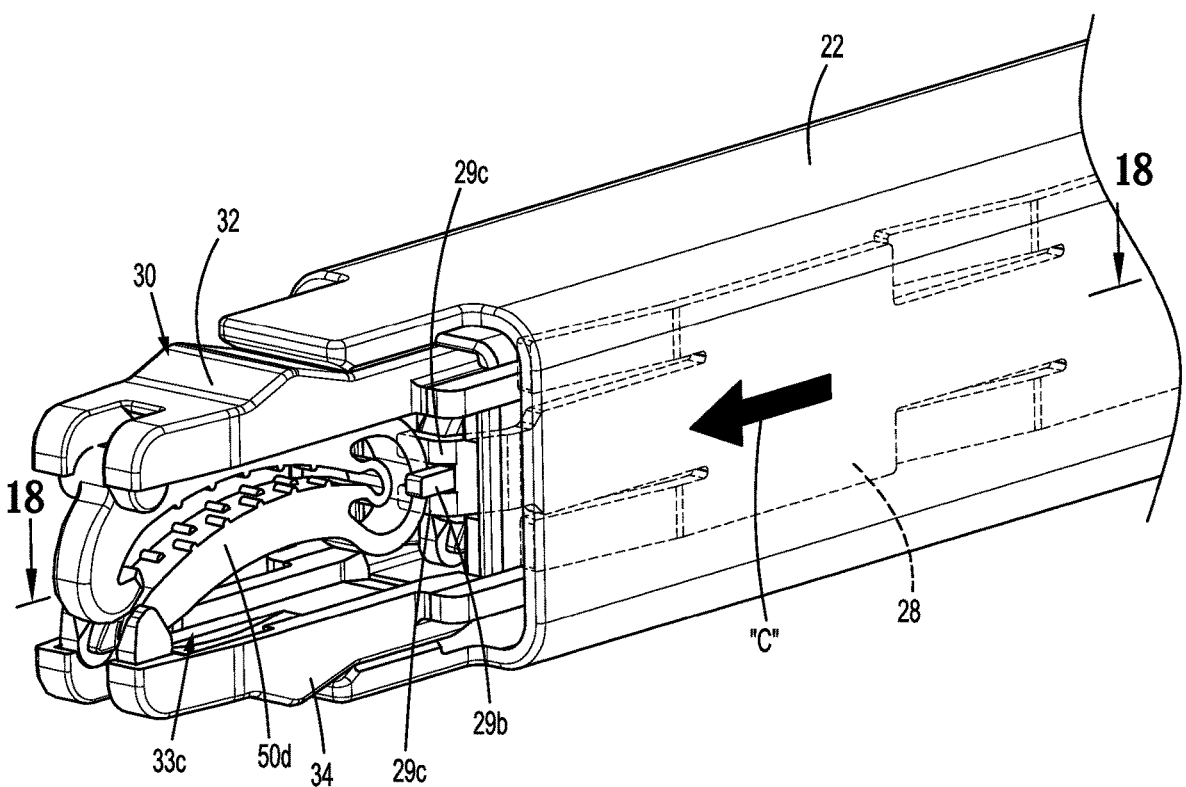
Figures 18, 19:
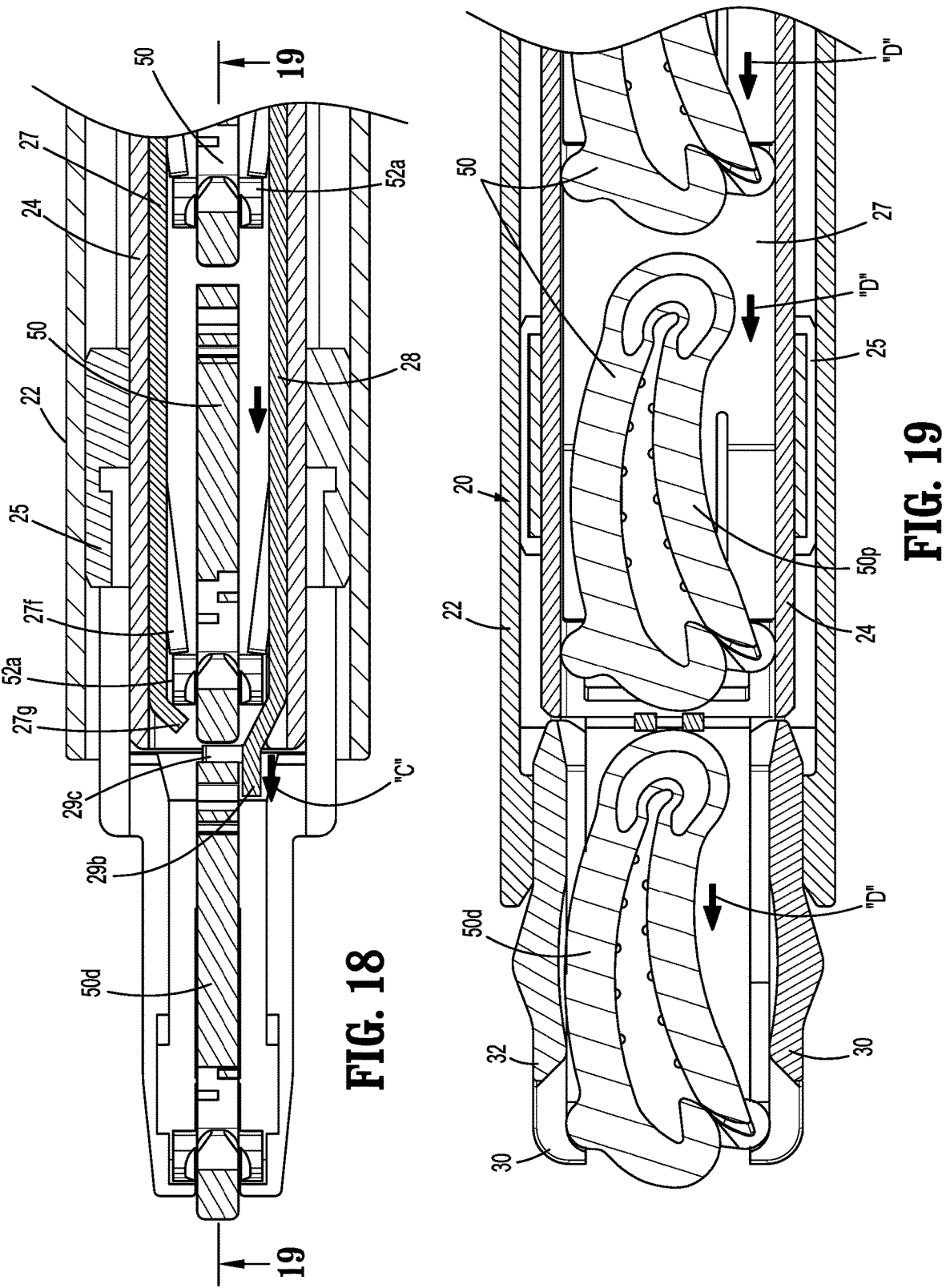

Movable tab assembly 28 of elongated shaft assembly 20 cooperates with stationary tab assembly 27 to support and advance clips 50 through ligation clip applier 1. Movable tab assembly is configured to move (e.g., translate) in an axial direction relative to stationary tab assembly 27. Movable tab assembly 28 is substantially structurally similar to stationary tab assembly 27 except movable tab assembly 28 includes a flexible finger assembly 29 (instead of an abutment) that extends distally from the central elongated rib 27*d* of a distal most tab section 27*b* of movable tab assembly 28. Flexible finger assembly 29 includes an angled base 29*a* that extends distally from central elongated rib 27*d* and is angled inwardly toward clips 50 at an acute angle from distal most tab section 27*b* of movable tab assembly 28. Flexible finger assembly 29 further includes a central linear digit 29*b* that extends distally from angled base 29*a* in an axial direction, and transverse digits 29*c* that are disposed on opposite sides of central linear digit 29*b*, and which extend in a transverse direction (e.g., across the longitudinal axis "L-L") relative to central linear digit 29*b* (see FIG. 8). Central linear digit 29*b* is configured to provide lateral support to a proximal end portion of the distal most clip 50*d* when clip 50*d* is supported between first and second jaw members 32, 34 (FIG. 17).

Jaw retainer 25 of elongated shaft assembly 20 includes segments 25*a*, which may be C or U-shaped (although any suitable shape may be provided), that connect together about inner tube 24 on a distal end portion thereof adjacent first and second jaw members 32, 34. As best seen in FIG. 9, each segment 25*a* includes spaced apart prongs 25*b* extending from a proximal end portion of an inner surface of the respective segment 25*a*. Prongs 25*b* are receivable within spacer slots 24*b* of inner tube 24 to secure segments 25*a* to the respective sides of inner tube 24. Each segment 25*a* defines support channels 25*c*, which may be T-shaped (although any suitable shape may be provided), in a distal end portion of the inner surface thereof. The support channels 25*c* are spaced apart from one another and positioned to receive proximal end portions of first and second jaw members 32, 34 therein for securing first and second jaw members 32, 34 to jaw retainer 25.

First and second jaw members 32, 34 of end effector 30 are substantially identical and each includes a jaw 33 having mounting legs 33*a* extending from a proximal end portion of jaw 33 to mounting feet 33*b* on a proximal end of mounting legs 33*a*. Mounting feet 33*b*, which may be T-shaped (although any suitable shape may be provided), are receivable within support channels 25*c* of jaw retainer 25 to secure first and second jaw members 32, 34 between inner tube 24 and jaw retainer 25. Jaw 33 has an inner surface 33*x* that defines a clip slot 33*c* configured to receive clips 50 therein and an outer surface 33*y* configured to engage teeth 22*c* of distal fingers 22*b* of outer tube 22. Clip slot 33*c* of inner surface 33*x* includes opposing lateral recess 33*d*, a clip trap 33*e* in a central distal end portion of jaw 33, and clip stop 33*f* at a distal end portion of jaw 33. Outer surface 33*y* of jaw 33 includes a proximal closing surface 33*p* and a distal clamping mound 33*z* configured to cooperate with distal fingers 22*b* of outer tube 22 for selectively approximating first and second jaw members 32, 34 together (e.g., closing and/or clamping thereof).

Each clip 50 of ligation clip applier 1 includes a first leg 52, a second leg 54, and a curved backspan 56 that pivotably connects first and second legs 52, 54 together on a proximal end portion thereof. First leg 52 includes a transverse guide rod 52*a* on an outer surface thereof and a hook 52*b* a distal end portion thereof. Second leg 54 includes distal guides 54*a* disposed on opposed side surfaces of second leg 54, and a catch 54*b* disposed between distal guides 54*a* and in registration with hook 52*b* of first leg 52. Distal guides 54*a* may have a pear or tear drop shape. First and second legs 52, 54 include a plurality of spaced apart grips 57 supported on inner surfaces thereof.

Figures 14, 15:
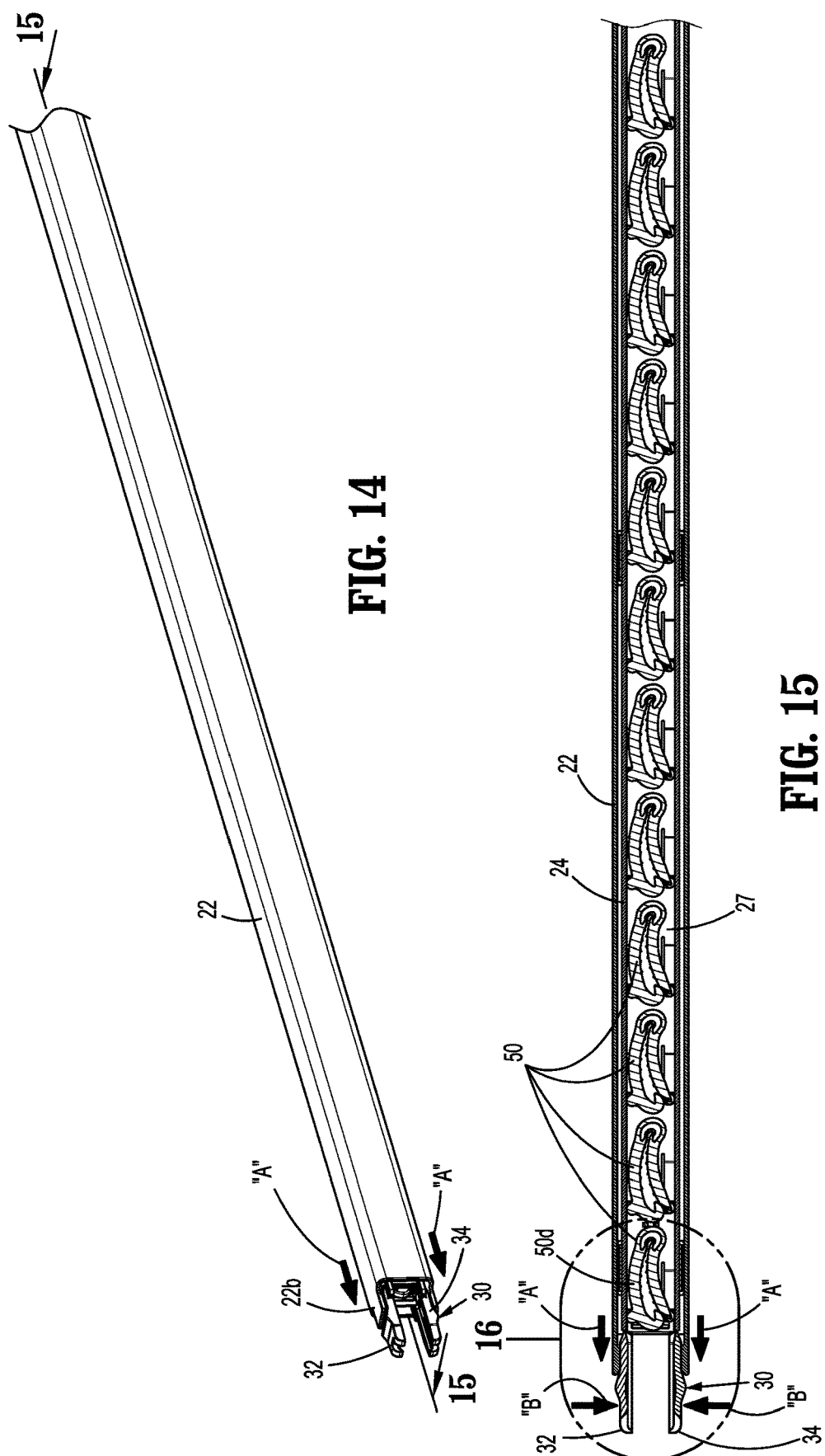
FIGS. 14-25 are progressive views illustrating the ligation clip applier of FIG. 1 being actuated for applying clips thereof to tissue.
Figure 16:
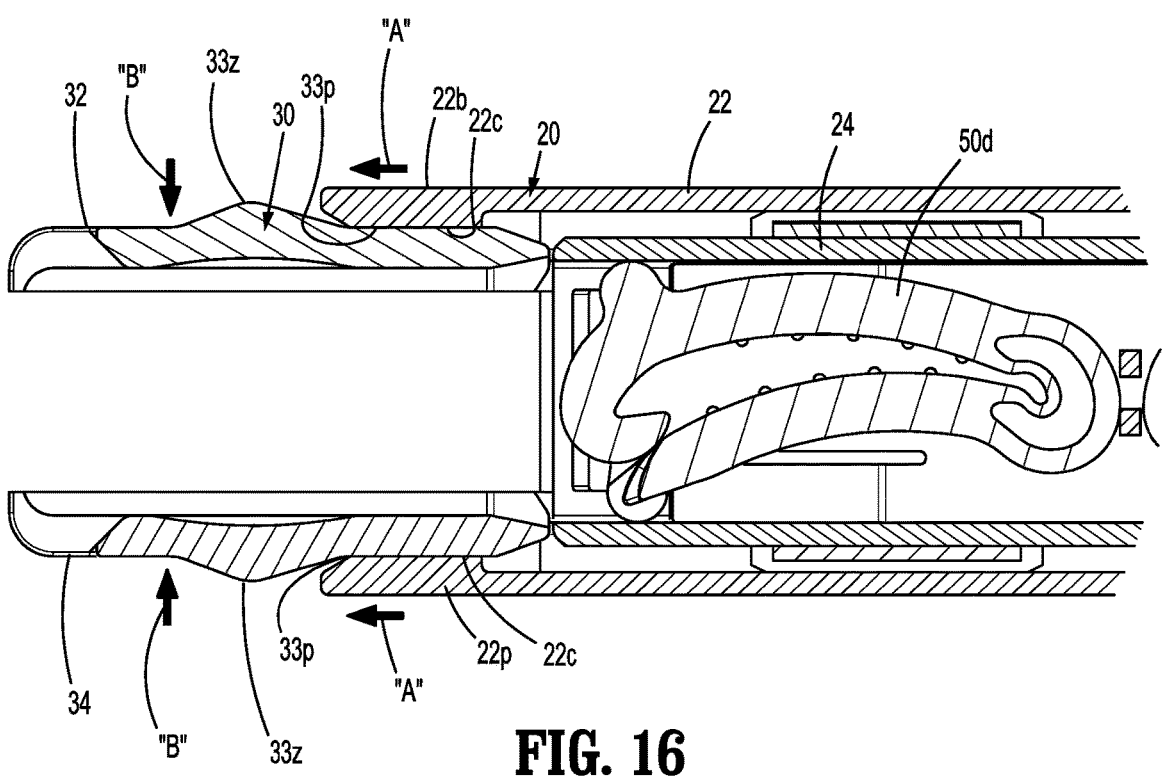

In use, outer tube 22 is advanced distally toward end effector 30, as indicated by arrows "A" shown in FIGS. 14-16, such that distal finger 22*b* of outer tube 22 cams over proximal closing surface 33*p* of first and second jaw members 32, 34 to cause first and second jaw members 32, 34 to pivot, from an open position thereof, toward one another, as indicated by arrows "B," and into a closed position thereof (FIG. 16). In the closed position, the first and second jaw members 32, 34 are disposed in a parallel and spaced-apart relationship to one another sufficient to receive the distal-most clip 50*d* of clips 50 therebetween. Movable tab assembly 28 can then be distally advanced relative to stationary tab assembly 27, as indicated by arrow "C" shown in FIGS. 17 and 18, to advance clips 50 distally, as indicated by arrows "D" shown in FIG. 19, so that distal-most clip 50*d* is received in clip slots 33*c* of first and second jaw members 32, 34. In particular, transverse digits 29*c* of finger assembly 29 contact and distally urge the proximal end of distal-most clip 50*d* while first and second tabs 27*e*, 27*f* of movable tab assembly 28 contact and distally urge transverse guide rod 52*a* of first leg 52 and distal guides 54*a* of second leg 54 of each respective clip 50 to distally advance clips 50 along inner tube 24 of elongated shaft assembly 20.

Figures 20, 21:
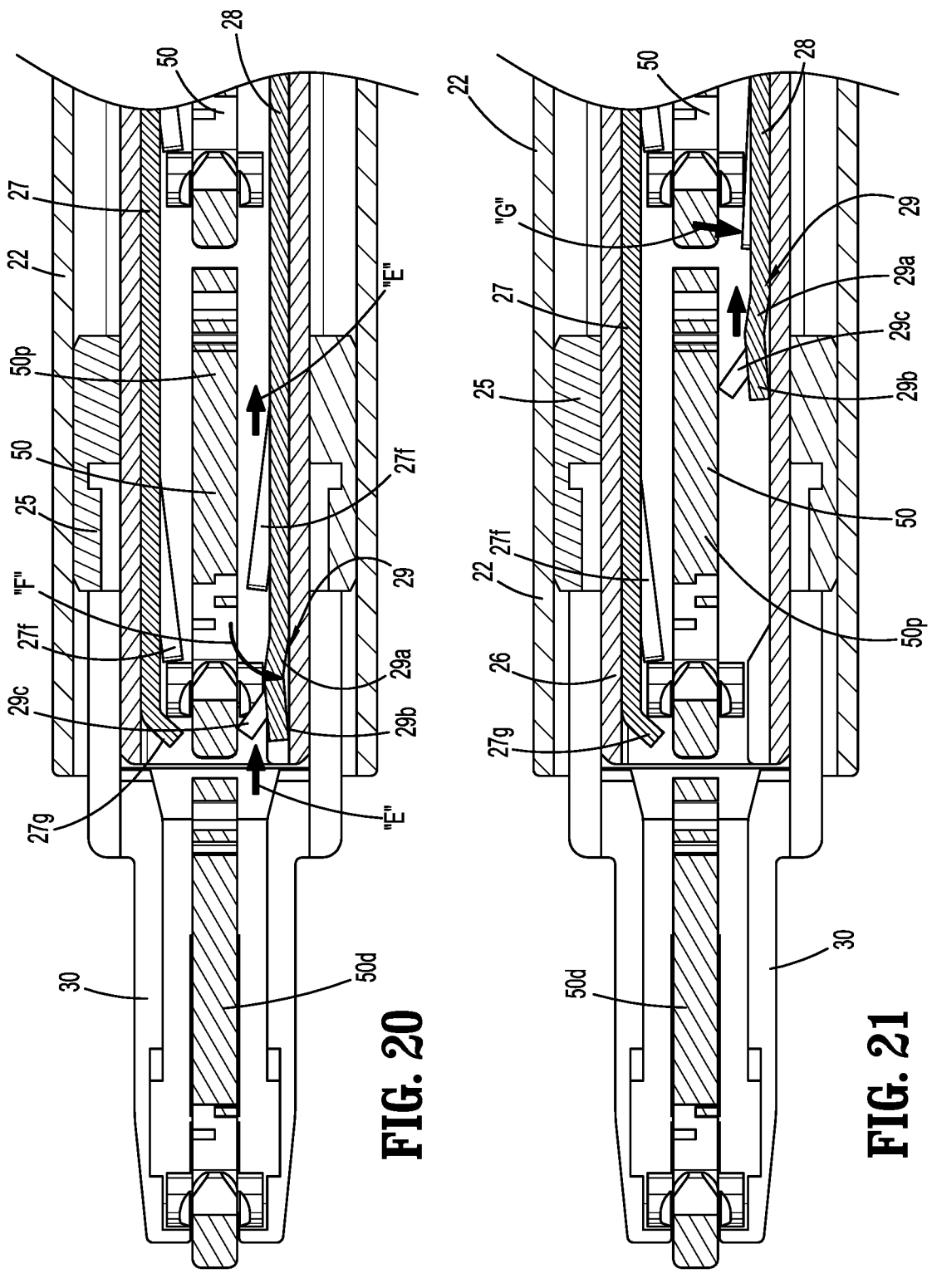

Once the distal-most clip 50*d* of clips 50 is fully seated within end effector 30 (e.g., where transverse guide rod 52*a* of first leg 52 and distal guides 54*a* of second leg 54 of distal-most clip 50*d* are engaged with clip stops 33*f* of first and second jaw members 32, 34), movable tab assembly 28 is then retracted proximally, as indicated by arrows "E" shown in FIG. 20. As movable tab assembly 28 retracts, a distally penultimate clip 50*p* engages flexible finger assembly 29 and causes flexible finger assembly 29 to pivot or flex outwardly about the distal end of central elongated rib 27*d* to which flexible finger assembly 29 is mounted, as indicated by arrow "F" shown in FIG. 20. Further retraction causes, first and second tabs 27*e*, 27*f* of each tab sections 27*b* of movable tab assembly 28 to engage a respective one of the remaining clips 50 (namely, the respective transverse guide rod 52*a*, distal guides 54*a* thereof) that are proximal to the penultimate clip 50*p* so that the respective first and second tabs 27*e*, 27*f* likewise pivot or flex outwardly about the respective bases 27*a* thereof, as indicated by arrow "G" shown in FIG. 21. Once, movable tab assembly 50 retracts proximally a length of one clip of clips 50, flexible finger assembly 29 and all first and second tabs 27*e*, 27*f* of movable tab assembly 28 are urged back or biased toward an initial or unflexed position, as indicated by arrows "H" and "I," respectively, so that transverse digits 29*c* of flexible finger assembly 29 is in contact with the proximal end of distally penultimate clip 50*p* and first and second tabs 27*e*, 27*f* of movable tab assembly 28 are engaged with a respective one of the clips 50 proximal to the distally penultimate clip 50*p* as shown in FIG. 22 (e.g., transverse guide rod 52*a* and distal guides 54*a* thereof).

Figures 22, 23:
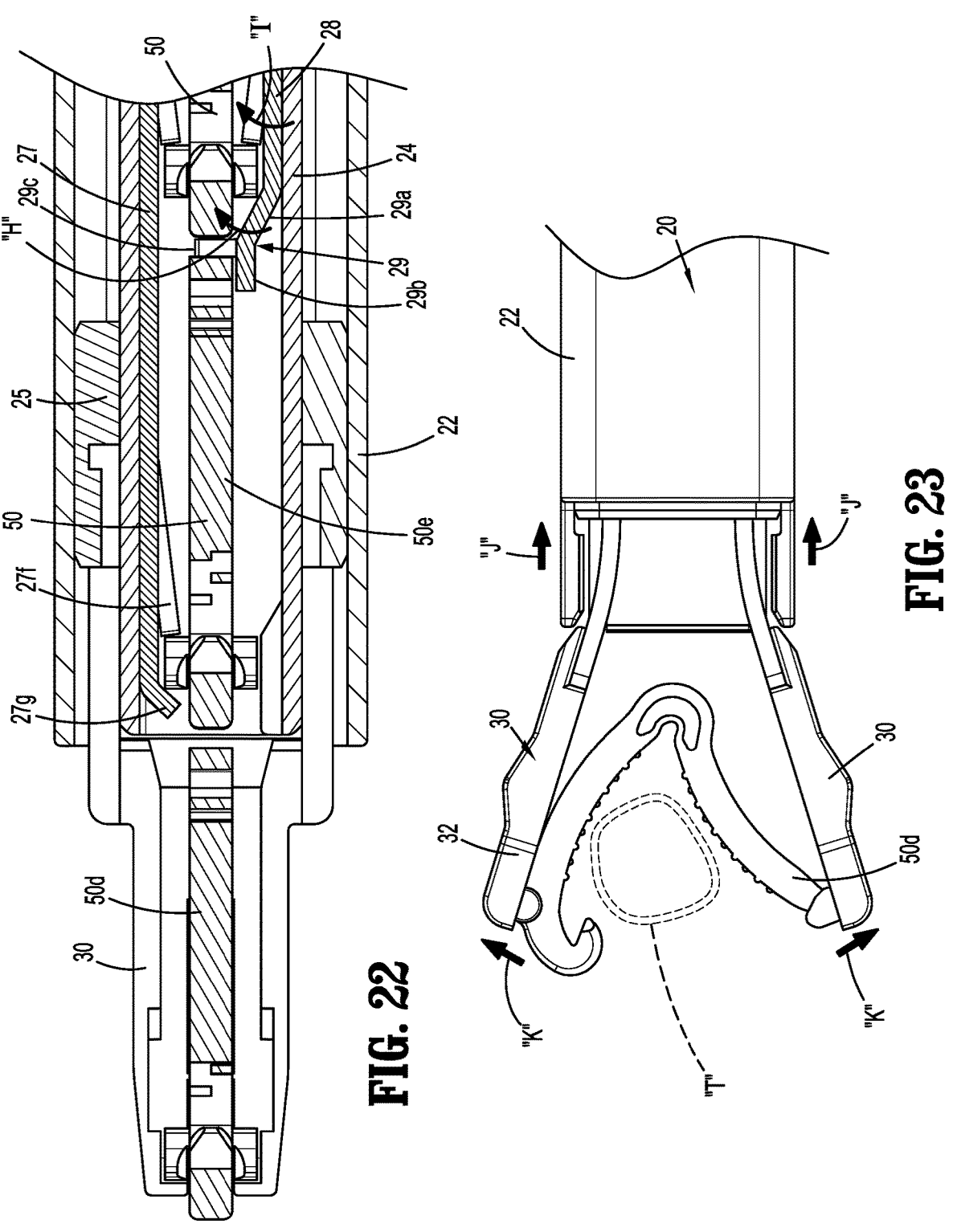
Figure 24:
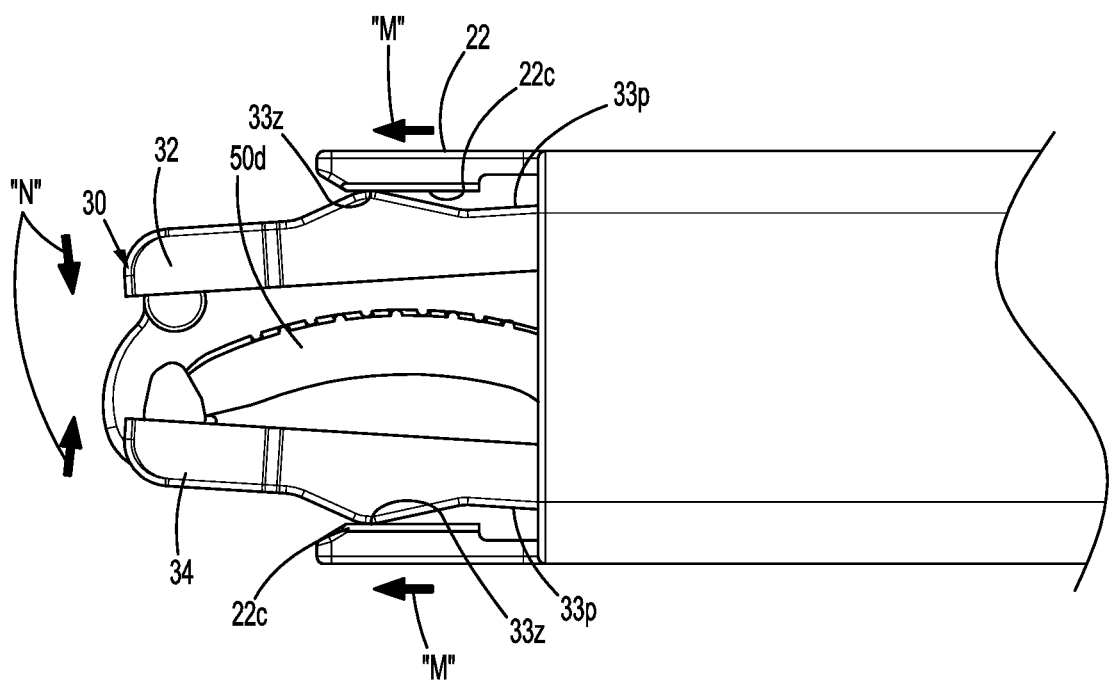
Figure 25:
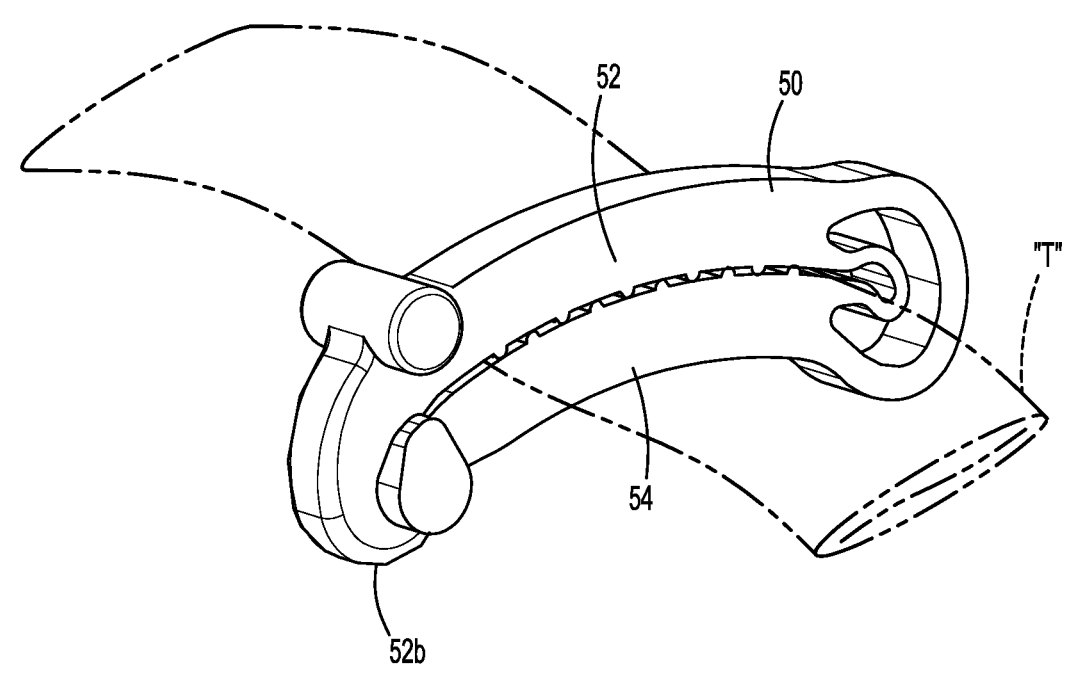
Figure 26:
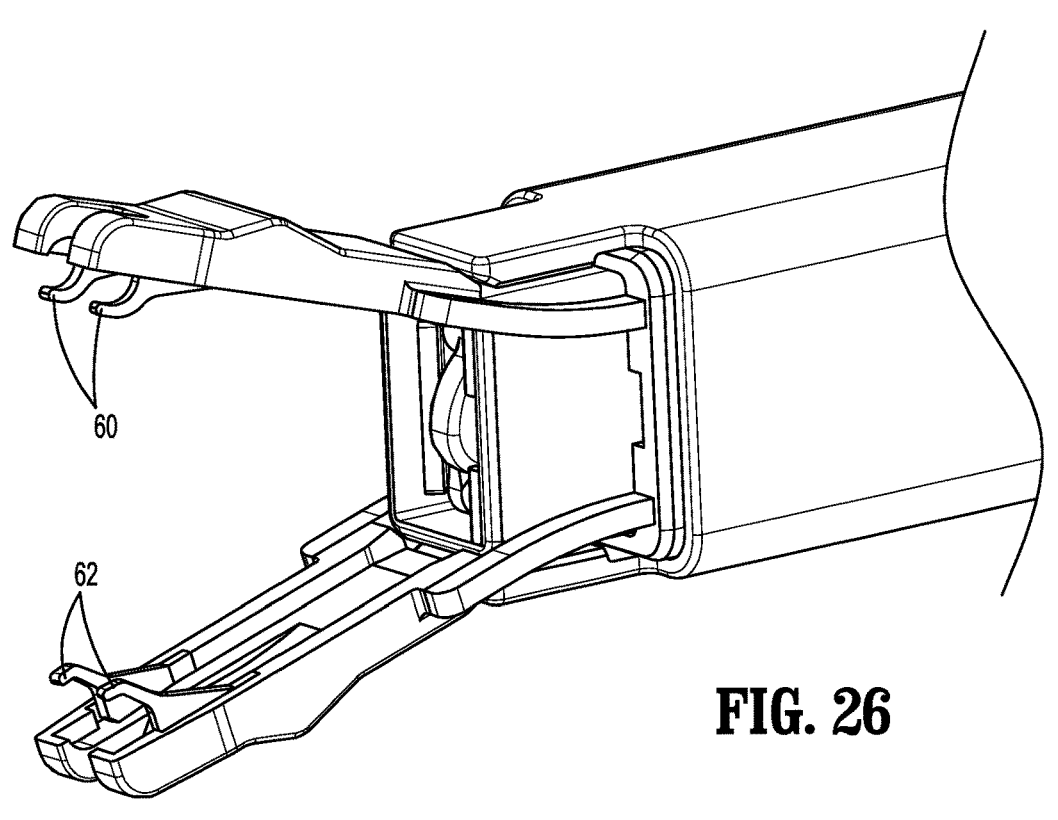
FIG. 26 is a perspective view of a distal end portion of another ligation clip applier according to exemplary aspects of the disclosure, the distal end portion having an end effector with jaw members thereof shown in an open position.
Figure 27:
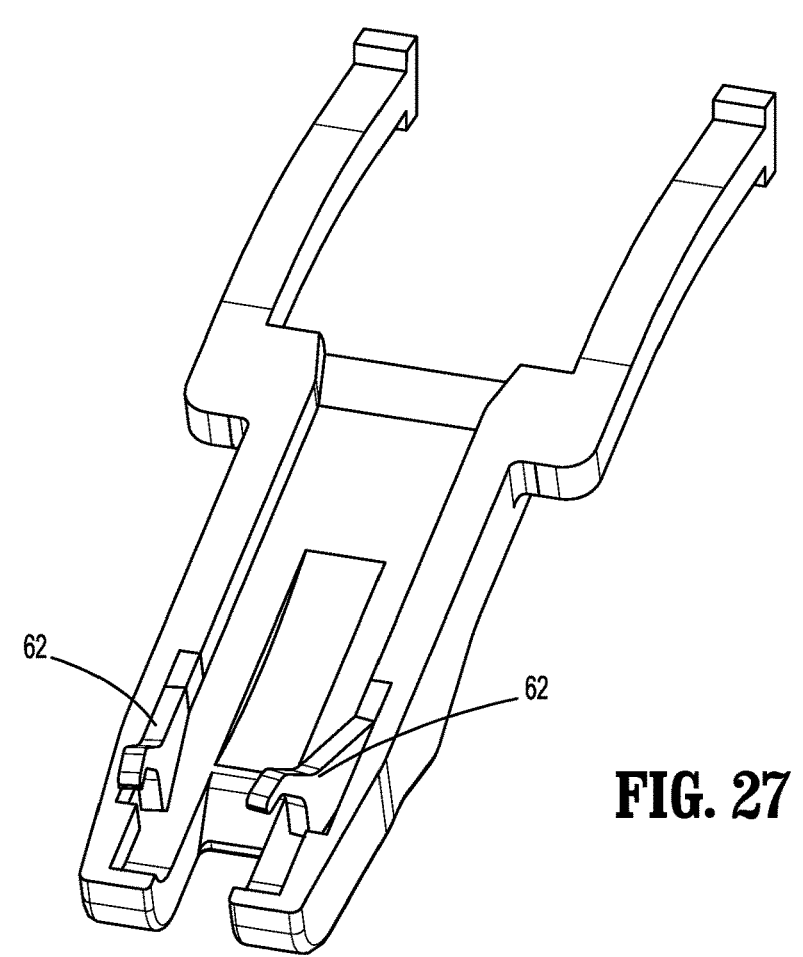
FIG. 27 is an enlarged, top, perspective view of a jaw member of the ligation clip applier of FIG. 26.
Figures 28, 29:
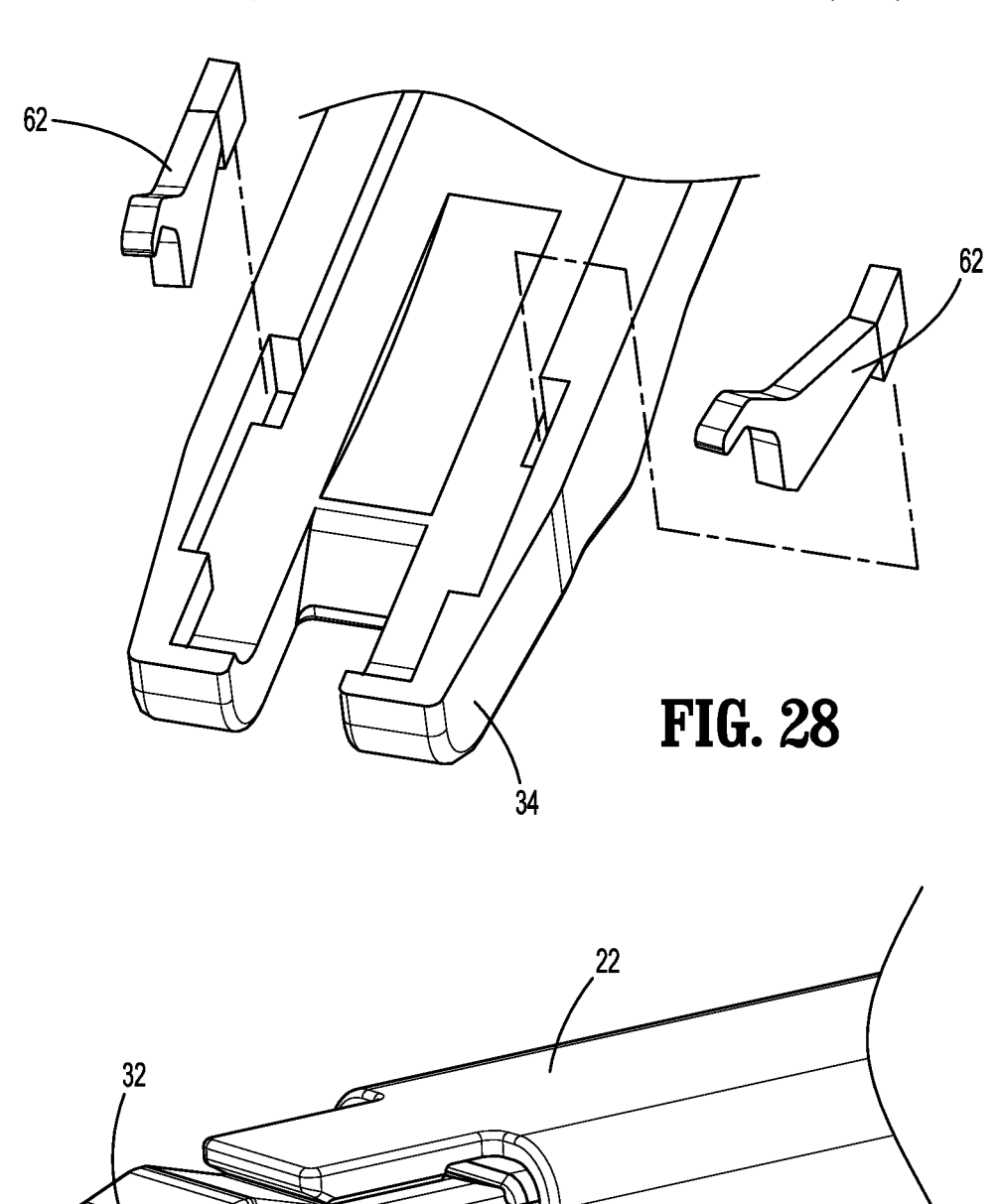
FIG. 28 is an enlarged, perspective view of a distal portion of FIG. 27, with parts separated.
FIG. 29 is a perspective view of the distal end portion of the ligation clip applier of FIG. 26 with the jaw members thereof shown in a closed position without a clip therebetween.
Figure 30:
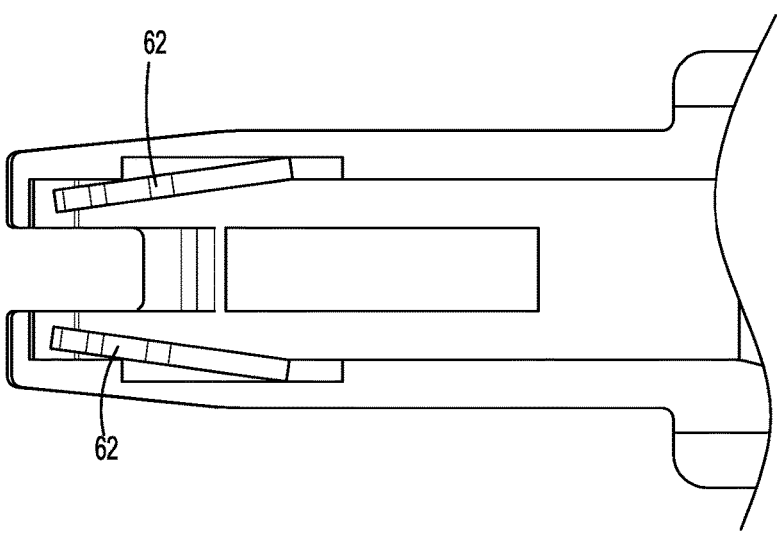
FIG. 30 is an enlarged, cross-sectional view as taken along section line 30-30 of FIG. 29.
Figure 31:
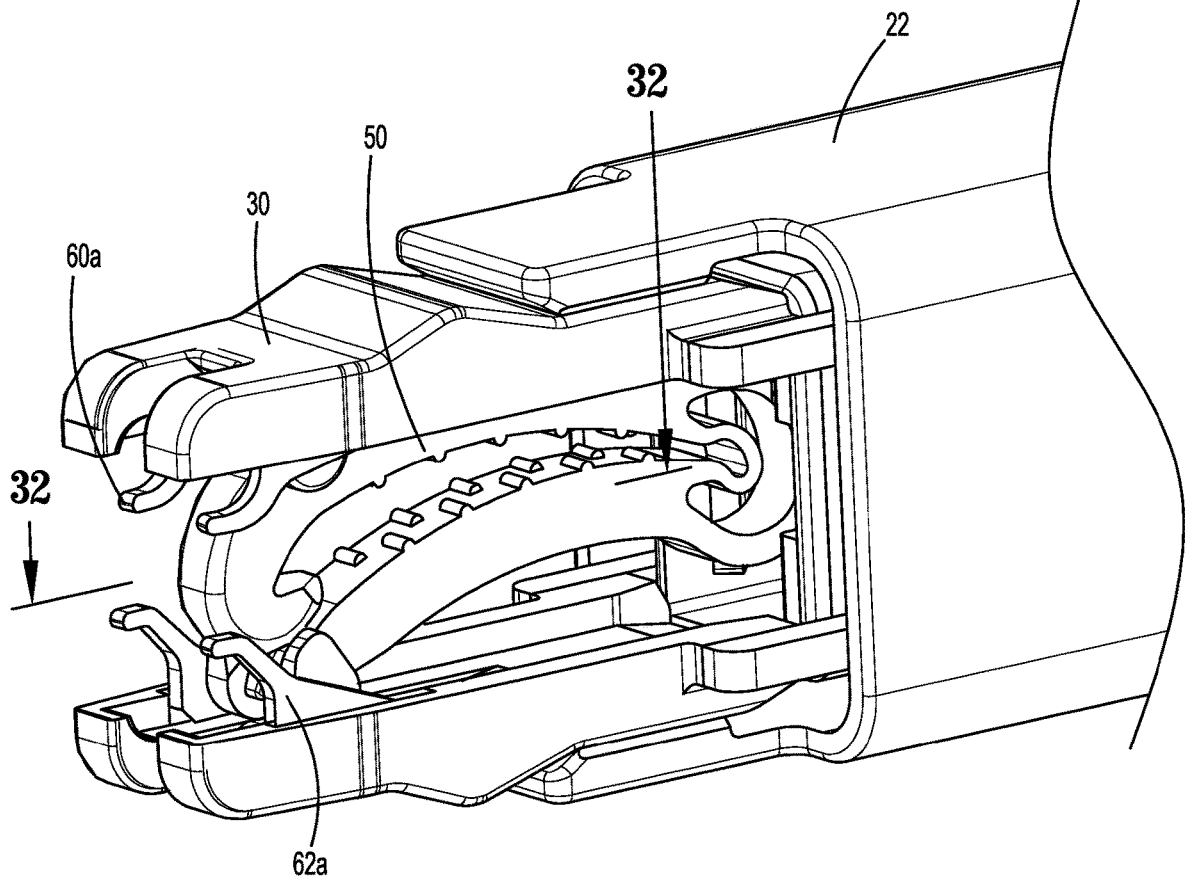
FIGS. 31-33 are progressive views illustrating a clip being advanced into the end effector of the ligation clip applier of FIG. 26 and between the jaw members.
Figure 32:
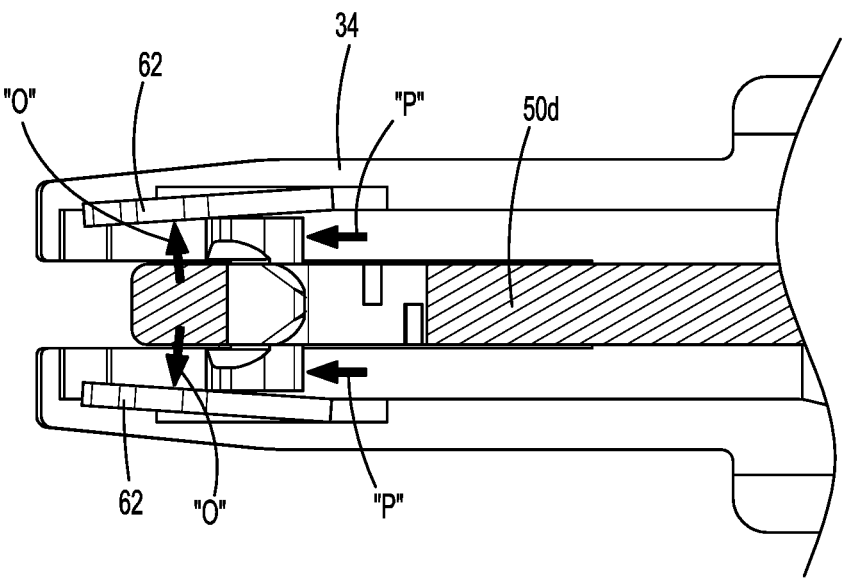

Then, outer tube 22 can be retracted proximally relative to end effector 30, as indicated by arrows "J" shown in FIG. 23, to enable first and second jaw members to move or pivot away from one another (e.g., open), as indicated by arrows "K," so that distal-most clip 50*d* can open for capturing tissue "T" therebetween. Outer tube 22 can then distally advanced distally toward end effector 30, as indicated by arrows "M" shown in FIG. 24, such that distal finger 22*b* of outer tube 22 cams over proximal closing surface 33*p* and distal clamping mound 33*z* of first and second jaw members 32, 34 to cause first and second jaw members 32, 34 to pivot, from an open position thereof, toward one another, as indicated by arrows "N," beyond a closed position (FIG. 16), and into a clamping position thereof (FIG. 24), so that hook 52*b* and catch 54*b* of distal-most clip 50*d* are interlocked to secure the tissue "T" between first and second legs 52, 54 of distal-most clip 50*d*. Outer tube 22 is then retracted proximally relative to end effector 30 to enable first and second jaw members 32, 34 to pivot to the open position thereof for releasing distal-most clip 50*d* from ligation clip applier 1. This process can be repeated as desired to sequentially fire each clip 50 from ligation clip applier 1.

Figure 33:
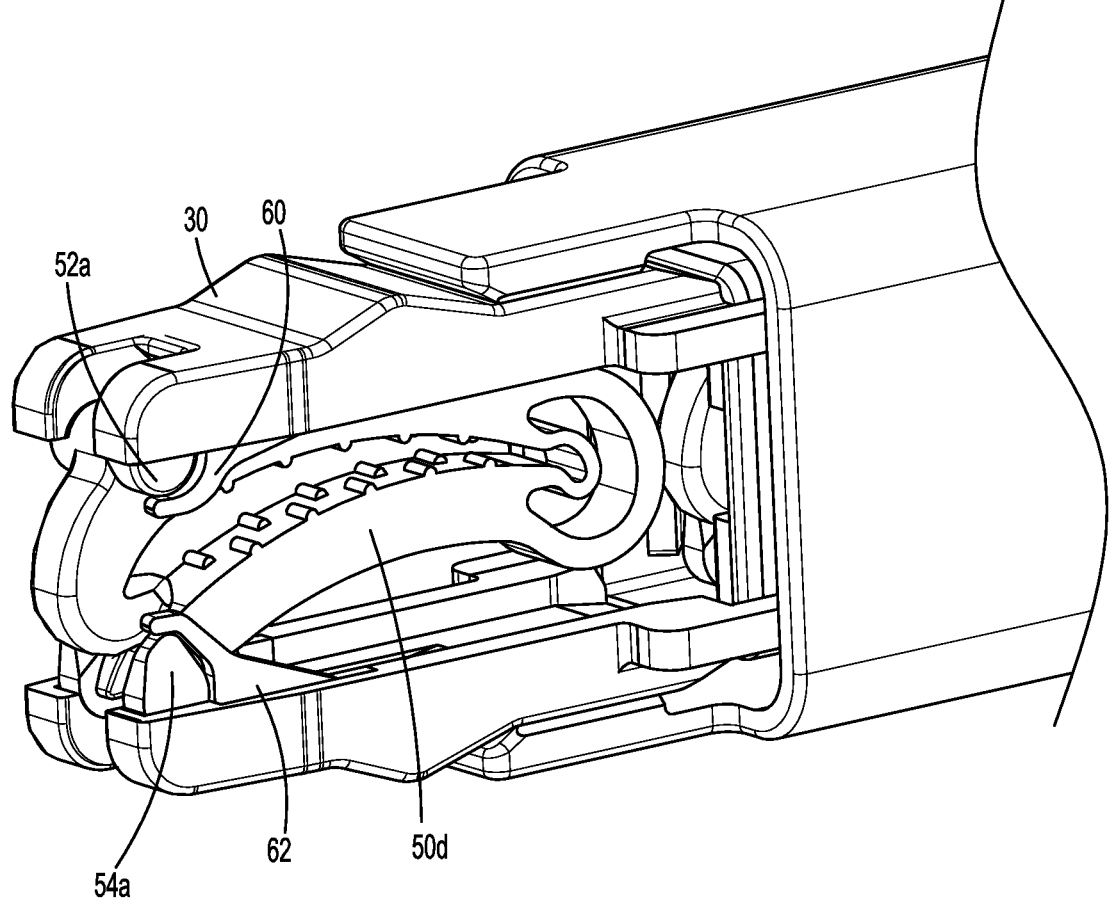
Figures 34, 35:
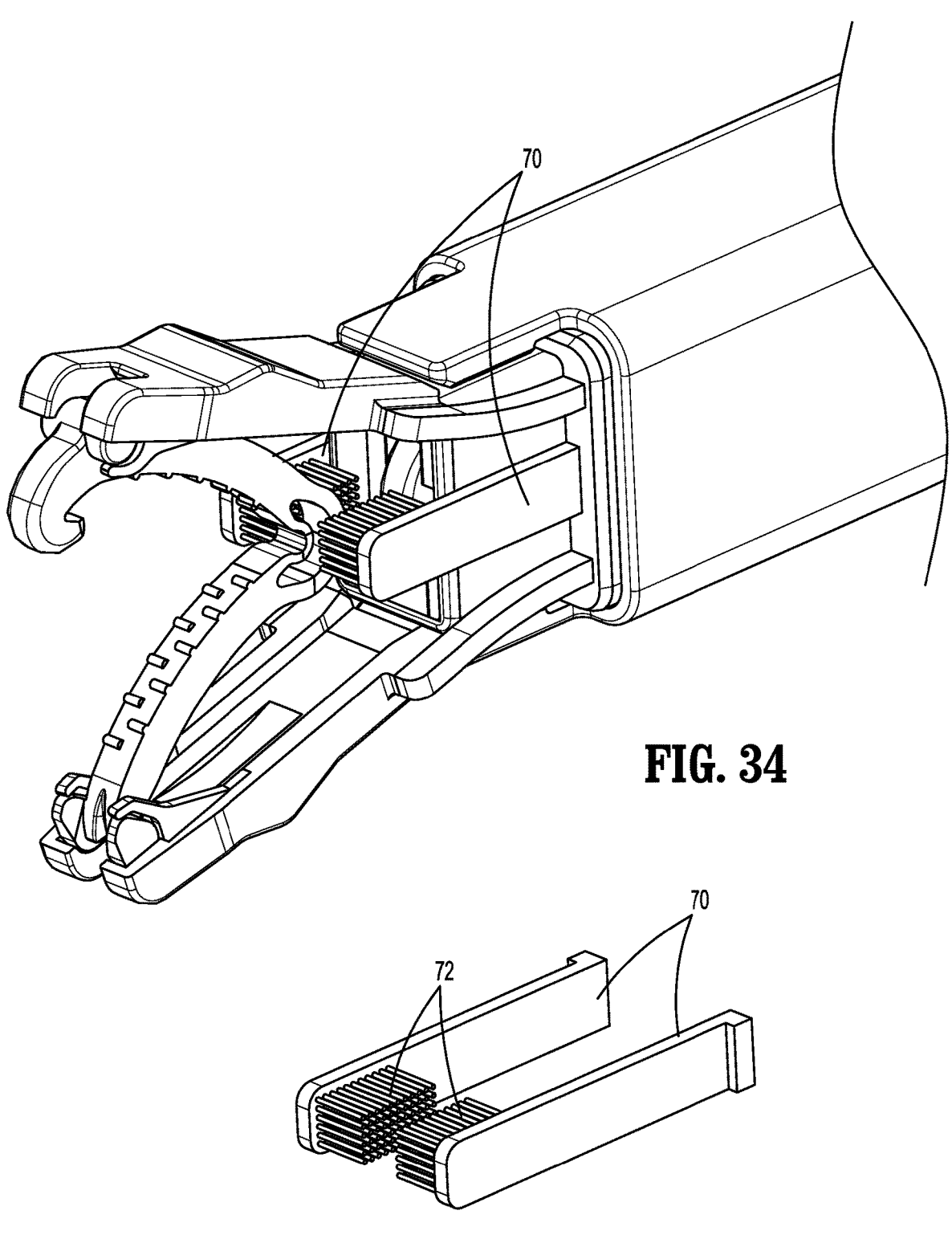
FIG. 34 is a perspective view of a distal end portion of yet another ligation clip applier according to exemplary aspects of the disclosure, the distal end portion having an end effector with jaw members thereof shown in an open position and supporting a clip therebetween in an open position thereof.
FIG. 35 is a perspective view of lateral stability members of the ligation clip applier of FIG. 34.
Figures 36, 37:
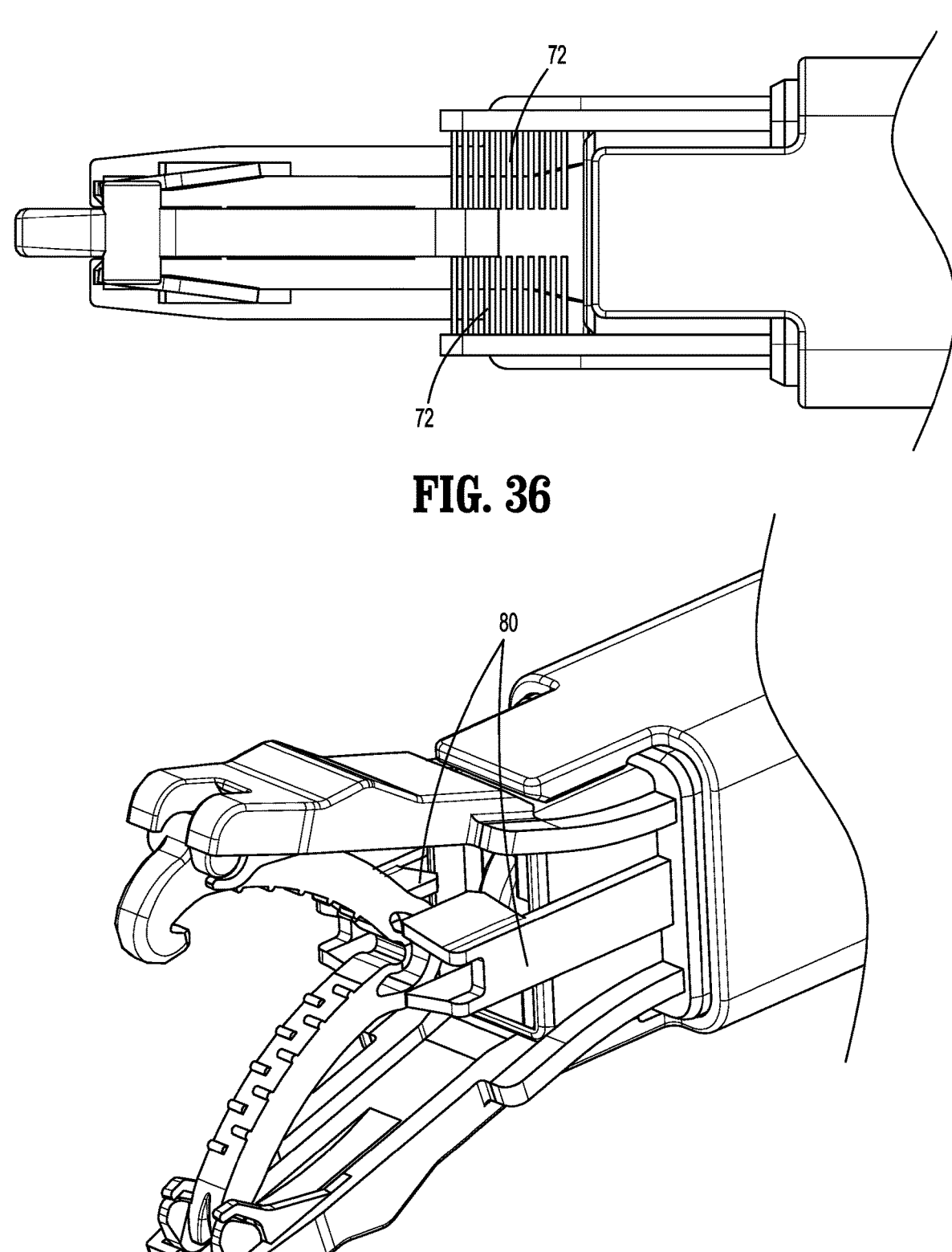
FIG. 36 is a top view of the distal end portion of the litigation clip applier of FIG. 34 with portions thereof removed for clarity.
FIG. 37 is a perspective view of a distal end portion of still another ligation clip applier according to exemplary aspects of the disclosure, the distal end portion having an end effector with jaw members thereof shown in an open position and supporting a clip therebetween in an open position thereof.
Figure 38:
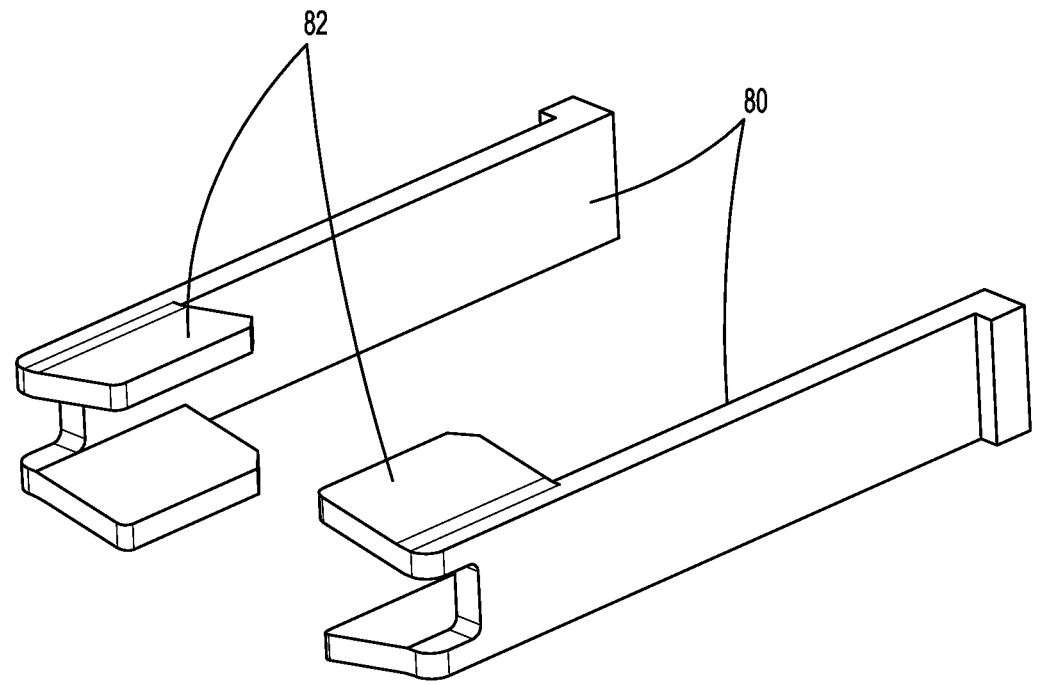
FIG. 38 is an enlarged, perspective view of lateral stability members of the ligation clip applier of FIG. 37.
Figure 39:
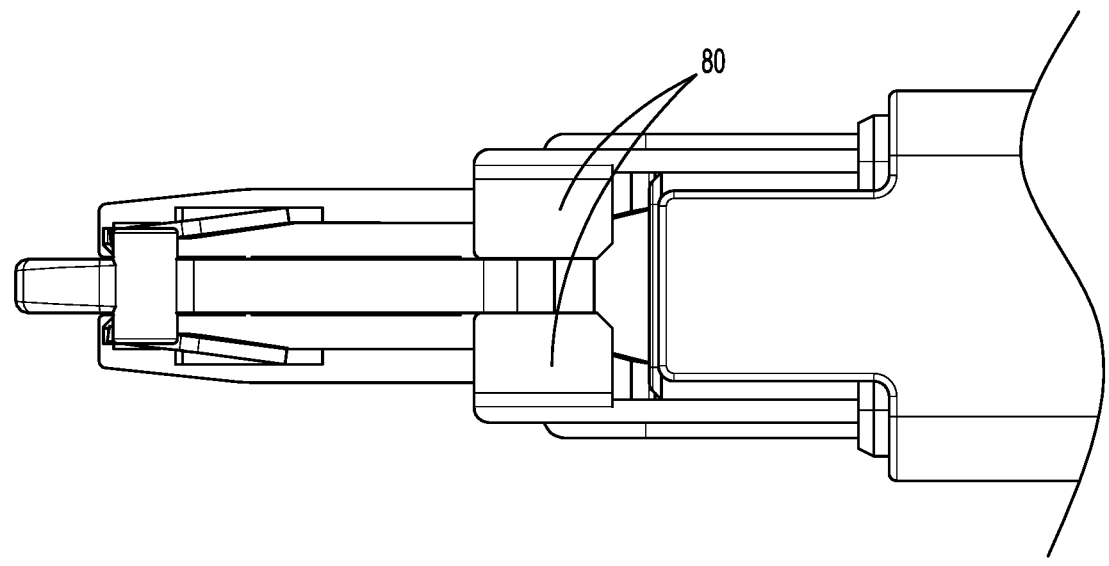
FIG. 39 is a top view of the distal end portion of the litigation clip applier of FIG. 37 with portions thereof removed for clarity.
Figures 40, 41:
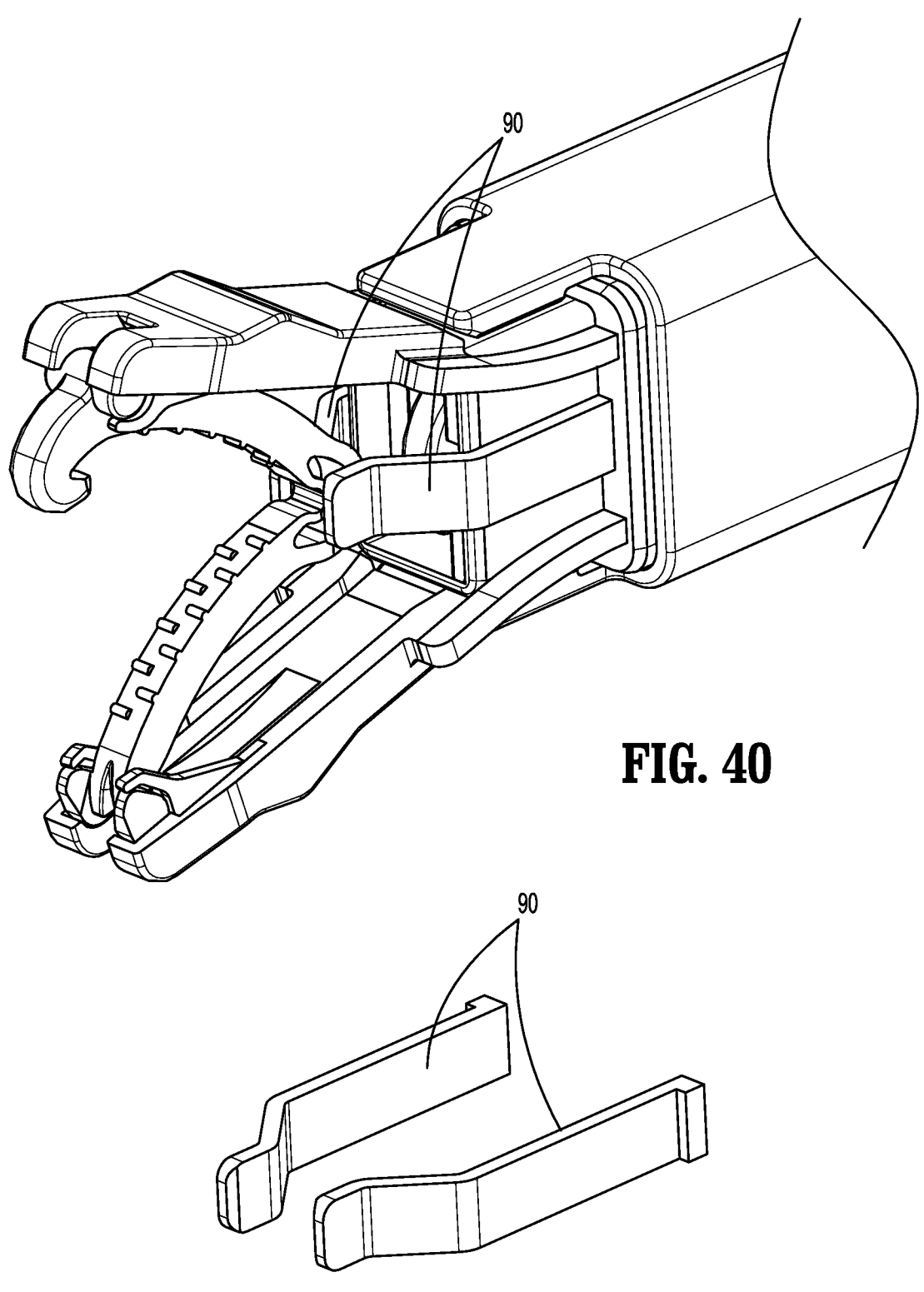
FIG. 40 is a perspective view of a distal end portion of one ligation clip applier according to exemplary aspects of the disclosure, the distal end portion having an end effector with jaw members thereof shown in an open position and supporting a clip therebetween in an open position thereof.
FIG. 41 is an enlarged, perspective view of lateral stability members of the ligation clip applier of FIG. 40.
Figure 42:
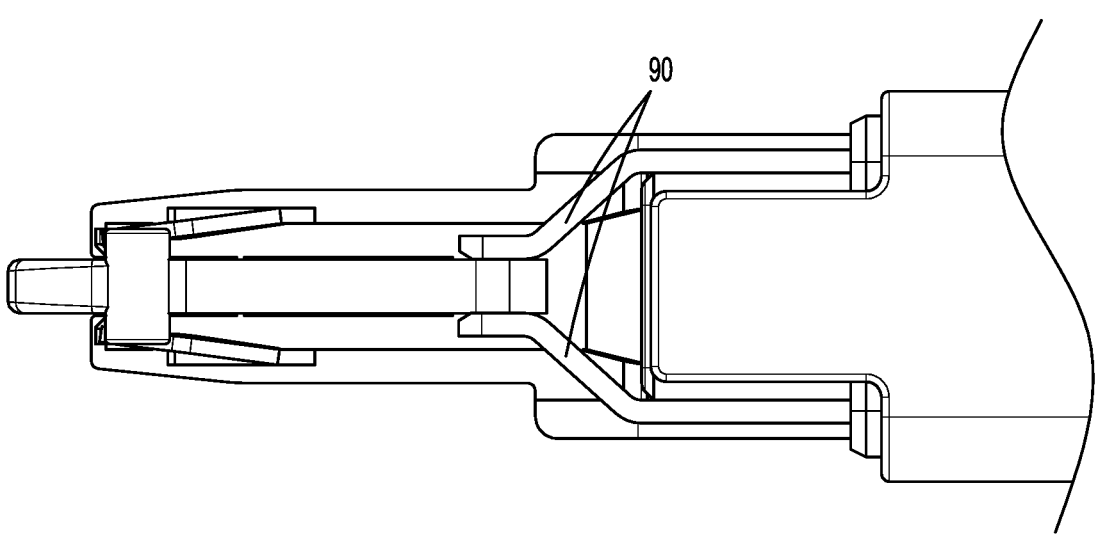
FIG. 42 is a top view of the distal end portion of the litigation clip applier of FIG. 40 with portions thereof removed for clarity.
Figure 43:
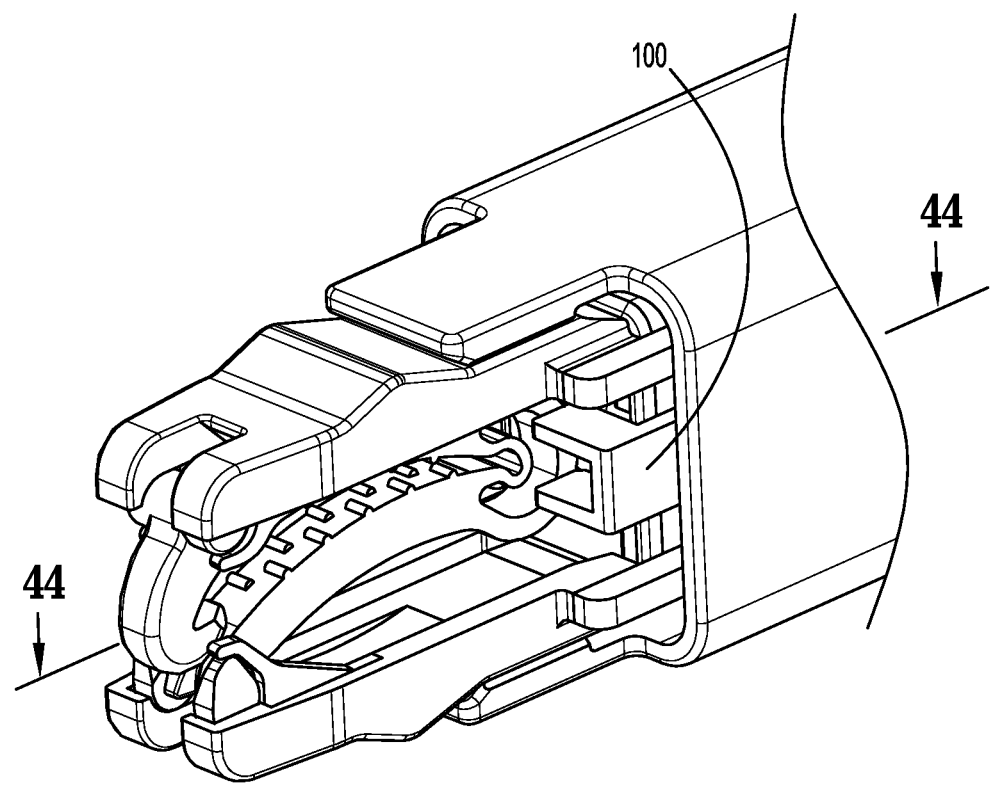
FIG. 43 is a perspective view of a distal end portion of another ligation clip applier according to exemplary aspects of the disclosure, the distal end portion having an end effector with jaw members thereof shown in a closed position and supporting a clip therebetween in a closed position thereof.
Figure 44:
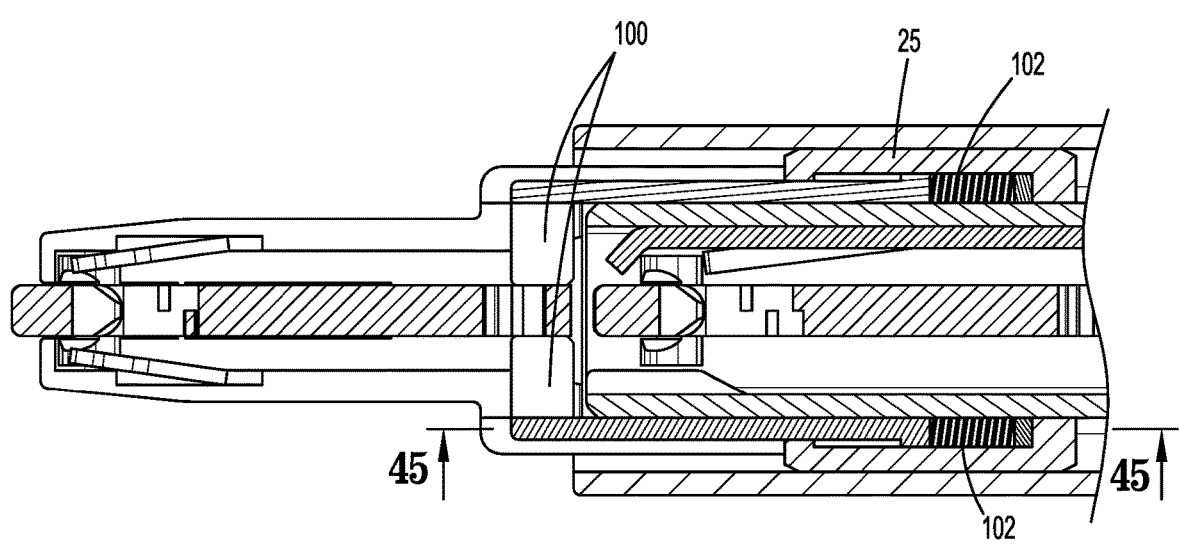
FIG. 44 is a cross-sectional view of FIG. 43 as taken along section line 44-44.
Figure 45:
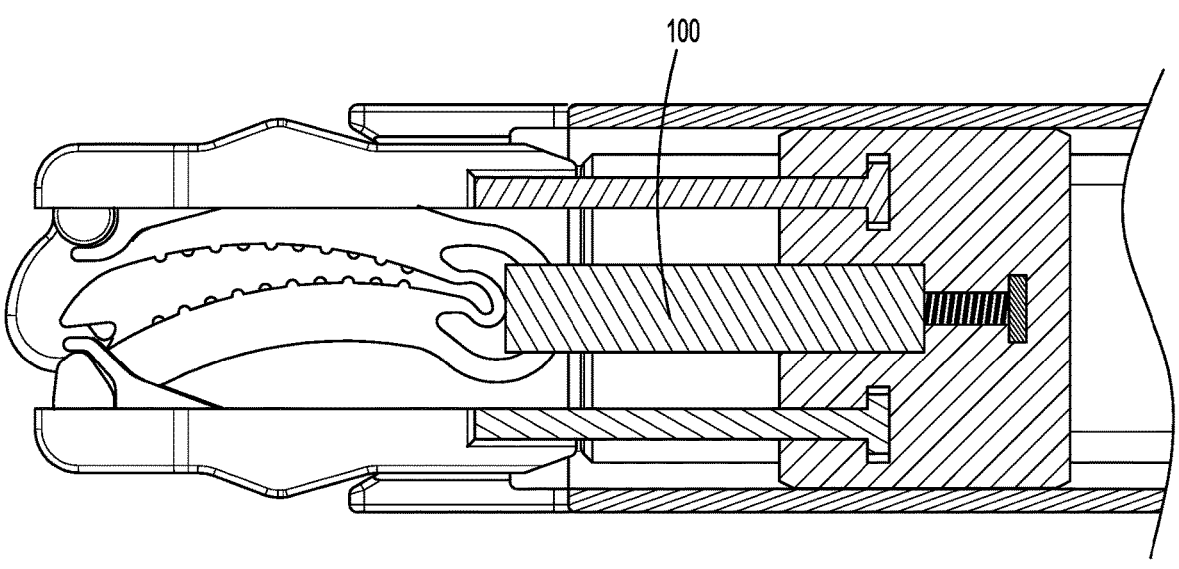
FIG. 45 is a cross-sectional view of FIG. 44 as taken along section line 45-45.

With reference to FIGS. 26-33, end effector 30 can include flexible retainers 60, 62 that are supported within first and second jaw members 32, 34 for supporting clips 50 within end effector 30. Flexible retainer 60 includes a hook 60*a* that is configured to engage transverse guide rod 52*a* of clips 50 and flexible retainer 62 includes a hook 62*a* that is configured to engage distal guides 54a. To enable distal-most clip 50d to fully seat within end effector 30, flexible retainers 60, 62 are configured to flex or pivot outwardly, as indicated by arrows "O," so transverse guide rod 52a and distal guides 54a of distal-most clip 50d can be advanced into end effector 30 and distally past flexible retainers 60, 62, as indicated by arrows "P" shown in FIG. 32. Flexible retainers 60, 62 will bias or pivot inwardly back to an initial or unflexed position thereof, once distal-most clip 50d is fully seated within end effector 30, as seen in FIG. 33. These retainers 60 are configured to retain clips 50 in end effector 30 and to limit movement of clips 50 with respect to first and second jaw members 32, 34 in longitudinal (e.g., proximal—distal) and vertical (e.g., from first to second jaw members 32, 34 or vice versa) directions. These retainers 60 are sufficiently strong to retain transverse guide rod 52a and distal guides 54 of clips 50 prior to a closing of such clip 50. These retainers 60 are also sufficiently resilient to bend/deflect.

Figure 46:
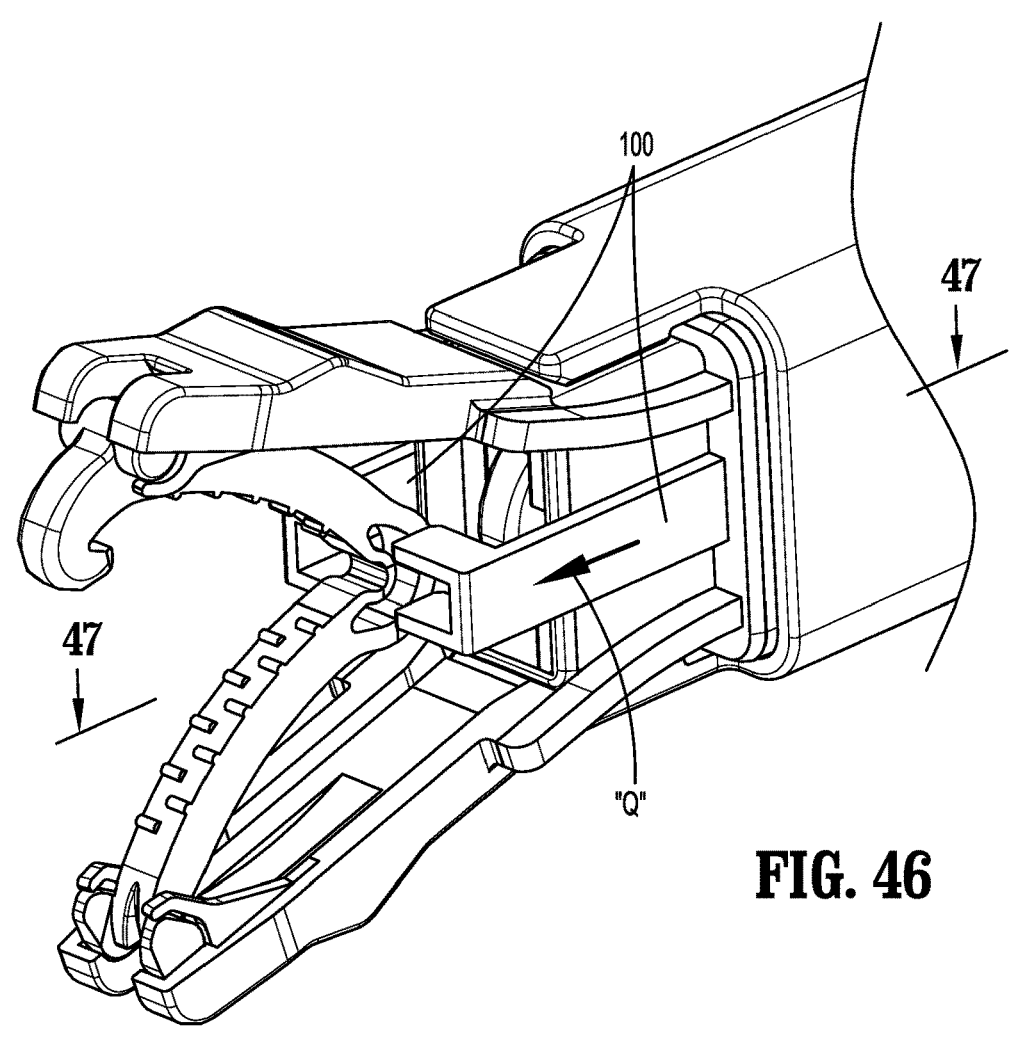
FIG. 46 is a perspective view of a distal end portion of still another ligation clip applier according to exemplary aspects of the disclosure, the distal end portion having an end effector with jaw members thereof shown in an open position and supporting a clip therebetween in an open position thereof.
Figure 47:
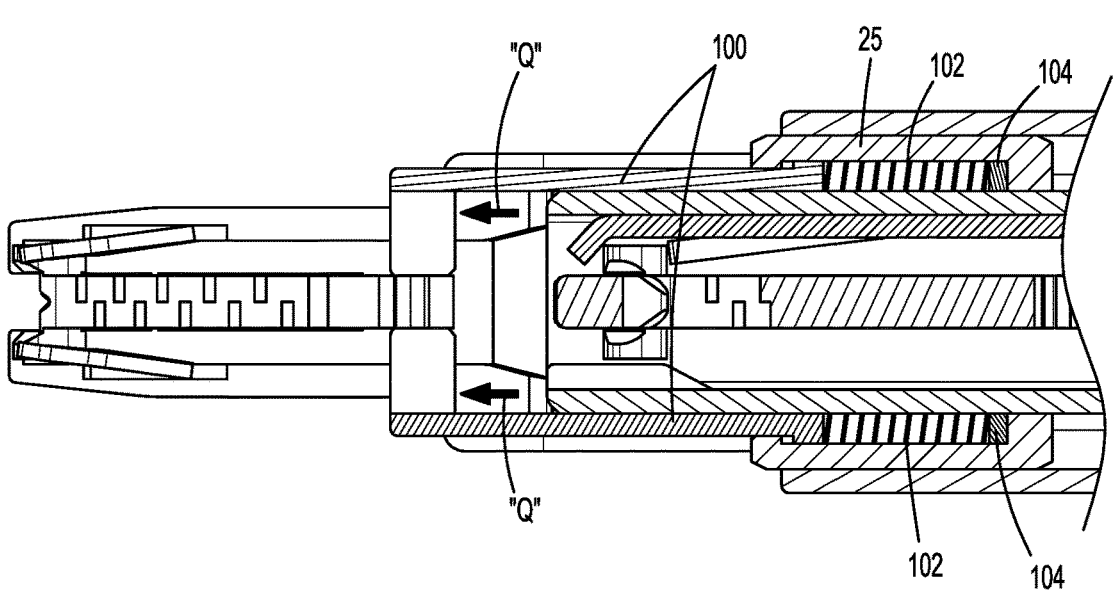
FIG. 47 is a cross-sectional view of FIG. 46 as taken along section line 47-47.
Figure 48:
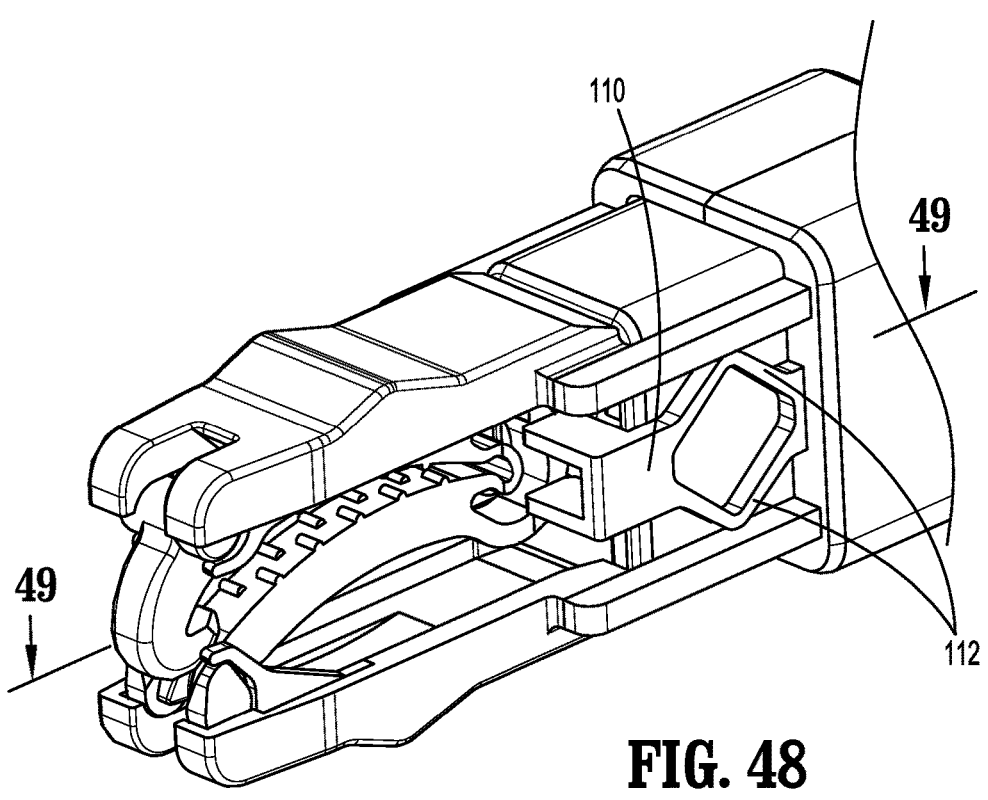
FIGS. 48-51 are progressive view of a distal end portion of yet another ligation clip applier according to exemplary aspects of the disclosure.
Figure 49:
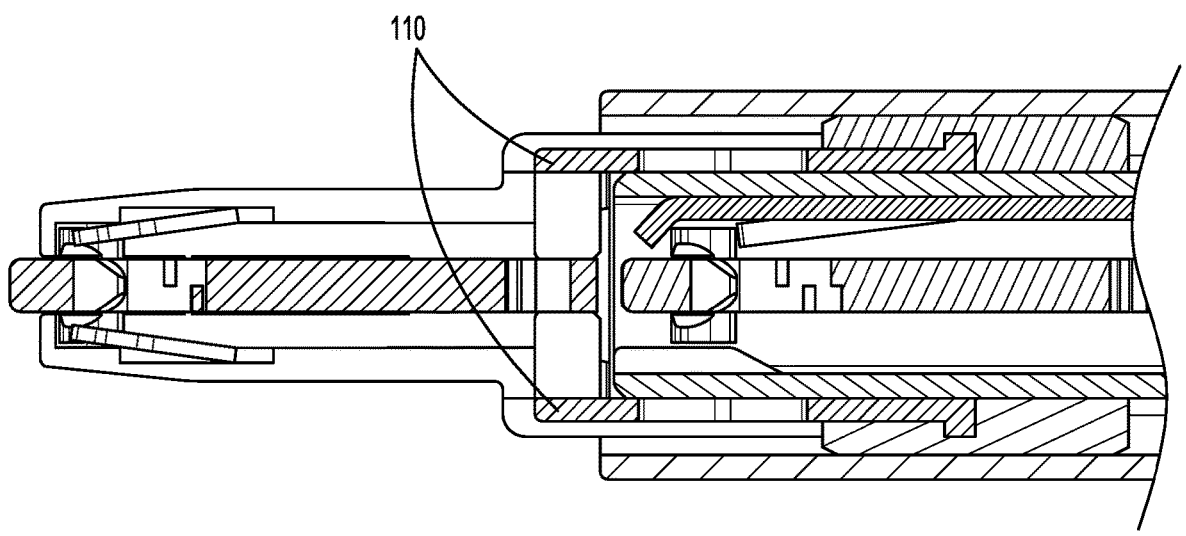
Figures 50, 51:
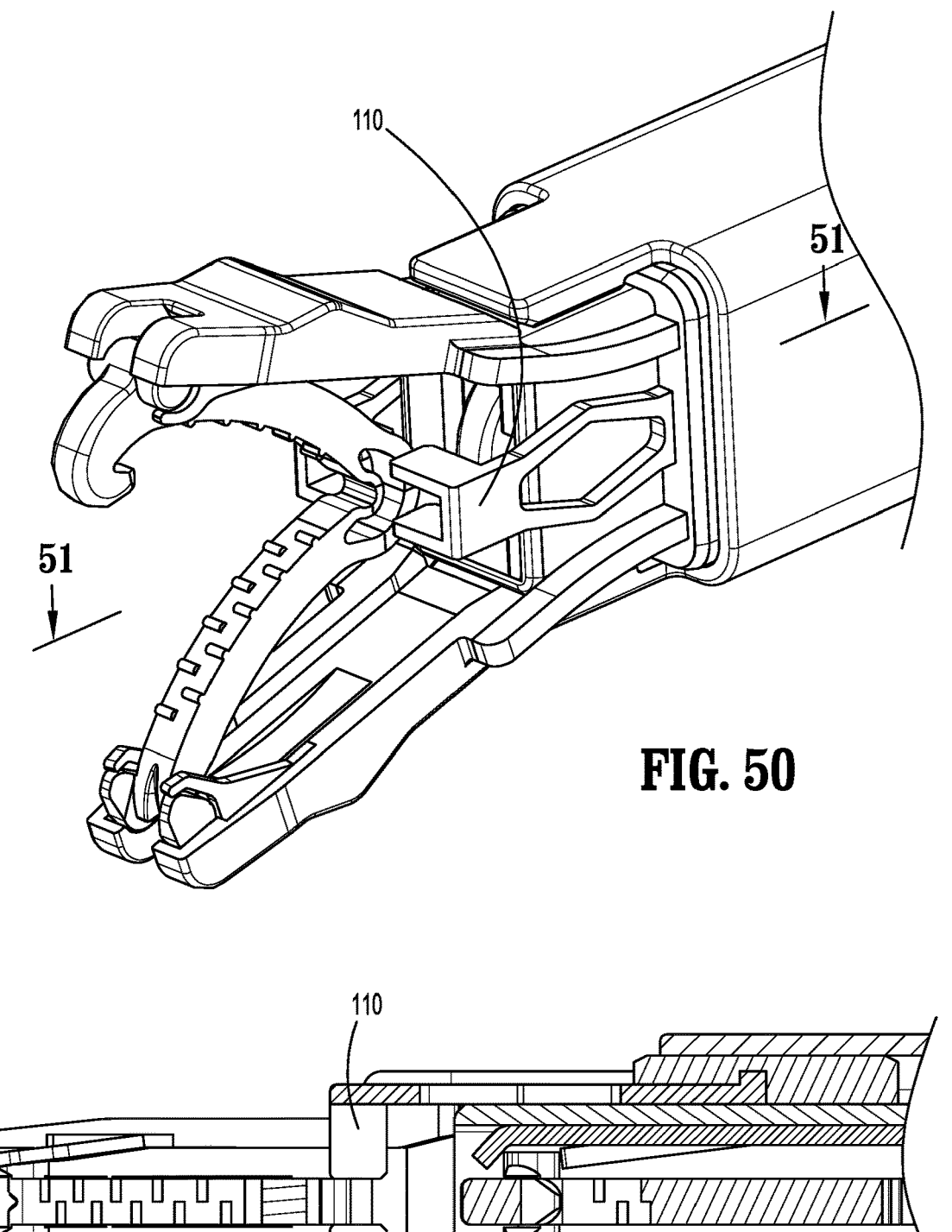

As seen in FIGS. 34-51, the ligation clip applier 1 can further include lateral stability arms, such as lateral stability arms 70, 80, 90, 100, and 110 that provide lateral support to a proximal end portion of the distal-most clip 50d supported in end effector 30 through a range of clip movement (e.g., translation of clip 50). Advantageously, these features also minimize impact on clip firing while maintaining lateral stability of clip. For instance, lateral stability arms 70 may include an array of spaced-apart transverse support bars 72 (e.g., brush-like) or a pair of spaced-apart flexible wings 82 that extend laterally from a distal end portion of arms 70 or 80. In aspects, lateral stability arms 100 may be coupled to the jaw retainer 25 and may be spring-biased by a spring 102 supported in the jaw retainer 25 (e.g., via retention block 104) to enable lateral stability arms 100 to translate between proximal and distal positions, as indicated by arrows "Q" shown in FIGS. 46 and 47, as clip 50 moves between proximal and distal positions. In some aspects, lateral stability arms 110 can include a compliant mechanism 112 (e.g., leaf springs) formed in the lateral stability arms 110 to enable arms 110 to move between extended (FIG. 50) and retracted positions (FIG. 48) as compliant mechanism 112, namely, segments thereof, move between elongated (FIG. 50) and retracted (FIG. 48) positions.

In aspects, the first and/or second jaw members may include stainless steel, spring steel, titanium, other metal, polymer, resilient polymer, or combination of materials. In aspects, the first and/or second jaw members may be machined, welded, stamped, metal injection molded, injection molded, additive manufactured, etc.

In aspects, the outer tube may include stainless steel, titanium, or other metal, and/or a combination of metal end components which interact with the first and/or second jaw members and may include a polymer and/or a composite material.

In aspects, the tube spacers may be polymer.

In aspects, the inner tube may include stainless steel, titanium, or other metal.

In aspects, the stationary tab assembly may include metal or polymer or composite.

In aspects, the moving tab assembly may include metal (e.g., stainless steel), a composite, and/or may be overmolded.

In aspects, the jaw retainers may be a polymer, a metal, a composite, and/or integral to the inner tube or another component.

In aspects, the spacers may include polymer (likely ultra-high molecular weight polyethylene (UHMWPE) for lubricity and wear resistance), metal, or even may be integral to the inner tube or another component.

In aspects, the retention features may be a resilient material (polymer, elastomer, spring metal, Nitinol, etc.) or combination of materials. Depending on the material and the jaw material, the retention features may be attached to the jaw member by weld, overmold, adhesive, mechanical means, etc., or combinations thereof.

In aspects, the lateral stability arms may include a resilient material such as polymer, elastomer, or combination of materials.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A ligation clip applier, comprising:
an end effector including a first jaw member and a second jaw member; and
an elongated shaft assembly defining a longitudinal axis and configured to support a plurality of clips, the elongated shaft assembly secured to the first jaw member and the second jaw member, the elongated shaft assembly including:
an outer tube and an inner tube supported within the outer tube, the outer tube movable relative to the inner tube to move the first jaw member and the second jaw member relative to one another; and
a stationary tab assembly and a movable tab assembly supported within the inner tube and configured to engage the plurality of clips, the movable tab assembly being axially movable relative to the stationary tab assembly to move the plurality of clips relative to the end effector, the movable tab assembly including:
a flexible finger assembly supported on a distal end portion of the movable tab assembly and positionable in a first position to load a first clip of the plurality of clips into the end effector when the movable tab assembly is advanced distally to a second position, the flexible finger assembly being pivotable relative to a second clip of the plurality of clips when the movable tab assembly is retracted proximally from the second position to the first position,
wherein the flexible finger assembly further comprises an angled base extending inwardly towards the longitudinal axis with respect to the movable tab assembly, a central linear digit extending distally from the angled base, and at least two transverse digits extending from the angled base in a direction perpendicular to the longitudinal axis.

2. The ligation clip applier of claim 1, wherein the first jaw member includes a first jaw and mounting legs extending proximally from the first jaw, the mounting legs coupled to a jaw retainer secured to the inner tube.

3. The ligation clip applier of claim 2, wherein the first jaw includes an inner surface defining a clip slot configured to support one clip of the plurality of clips at a time.

4. The ligation clip applier of claim 3, wherein the first jaw includes an outer surface having a proximal closing surface and a distal clamping mound being engageable with the outer tube.

5. The ligation clip applier of claim 4, wherein the outer tube includes a distal finger being engageable with the proximal closing surface to move the first jaw member from an open position to a closed position for supporting the one clip between the first jaw member and the second jaw member in an unclamped position.

6. The ligation clip applier of claim 5, wherein the distal finger is engageable with the distal clamping mound to move the first jaw member from the closed position to a clamping position for clamping a first leg and a second leg of the one clip together into a clamped position.

7. The ligation clip applier of claim 1, further comprising a lateral stability arm extending from the elongated shaft assembly and configured to engage a proximal end portion of the one clip.

8. The ligation clip applier of claim 1, wherein the movable tab assembly includes an elongated bar defining a plurality of interconnected tab sections, each tab section including a first tab that is angled inwardly toward the plurality of clips.

9. The ligation clip applier of claim 8, wherein each tab section further includes a second tab that is angled inwardly toward the plurality of clips and an elongated rib being disposed between the first and second tabs.

10. The ligation clip applier of claim 1, wherein the flexible finger assembly is configured to selectively load the second clip into the end effector when retracted back to the first position.

11. A surgical device, comprising:
an end effector including a first jaw member and a second jaw member; and
an elongated shaft assembly defining a longitudinal axis and configured to support a plurality of clips, the elongated shaft assembly secured to the end effector, the elongated shaft assembly including:
a tube movable relative to the end effector, the tube being engageable with the first jaw member and the second jaw member to clamp a first clip between the first jaw member and the second jaw member; and
a movable tab assembly supported within the tube and including:
a movable elongated bar defining a plurality of tab pairs configured to engage the plurality of clips, wherein each tab pair of the plurality of tab pairs extends from the movable elongated bar and includes a first tab and a second tab; and
a flexible finger assembly supported on a distal end portion of the movable elongated bar, the flexible finger assembly having an angled base extending inwardly towards the longitudinal axis with respect to the movable tab assembly, a central linear digit extending distally from the angled base, and at least two transverse digits extending from the angled base in a direction perpendicular to the longitudinal axis;
wherein the movable tab assembly is axially movable relative to the longitudinal axis to move the plurality of clips relative to the end effector, and wherein the flexible finger assembly of the movable tab assembly is positionable in a first position to load the first clip of the plurality of clips into the end effector when the movable tab assembly is advanced distally to a second position.

12. The surgical device of claim 11, wherein the first jaw member includes a first jaw and mounting legs extending proximally from the first jaw, the mounting legs coupled to a jaw retainer supported within the tube.

13. The surgical device of claim 12, wherein the first jaw includes an inner surface defining a clip slot configured to support the first clip of the plurality of clips.

14. The surgical device of claim 13, wherein the first jaw includes an outer surface having a proximal closing surface and a distal clamping mound engageable with the tube.

15. The surgical device of claim 14, wherein the tube includes a distal finger engageable with the proximal closing surface to move the first jaw member from an open position to a closed position for supporting the first clip between the first jaw member and the second jaw member in an unclamped position.

16. The surgical device of claim 15, wherein the distal finger is engageable with the distal clamping mound to move the first jaw member from the closed position to a clamping position for clamping a first leg and a second leg of the first clip together into a clamped position.

17. The surgical device of claim 11, wherein the first jaw member and the second jaw member face each other in a first direction, wherein the longitudinal axis extends perpendicular to the first direction, and wherein the first tab and the second tab are aligned with one another in the first direction.

18. A surgical device, comprising:
a plurality of clips, each clip including a hook and a catch configured to interlock with one another;
a first jaw member;
a second jaw member; and
an elongated shaft assembly secured to the first jaw member and the second jaw member and defining a longitudinal axis, the elongated shaft assembly including:
a tube supporting the plurality of clips therein, the tube being selectively engageable with an outer surface of the first jaw member and the second jaw member to clamp a distal-most clip between the first jaw member and the second jaw member such that the hook and the catch of the distal-most clip interlock with one another; and
a tab assembly supported within the tube and including:
a movable elongated bar defining a plurality of angled tab pairs configured to engage with the plurality of clips for moving the plurality of clips through the tube in response to movement of the tab assembly relative to the tube, wherein each angled tab pair of the plurality of angled tab pairs extends from the movable elongated bar and includes a first angled tab and a second angled tab; and
a flexible finger assembly supported on a distal end portion of the movable elongated bar, the flexible finger assembly having an angled base extending inwardly towards the longitudinal axis with respect to the movable tab assembly, a central linear digit extending distally from the angled base, and at least two transverse digits extending from the angled base in a direction perpendicular to the longitudinal axis;
wherein the tab assembly is positionable to load the distal-most clip of the plurality of clips into the end effector when the tab assembly moves relative to the tube.

19. The surgical device of claim 18, wherein the second jaw member is positioned vertically above the first jaw member and wherein the first angled tab and the second angled tab are aligned with one another vertically.

20. The surgical device of claim 18, wherein the flexible finger assembly of the tab assembly is positionable in a first position to load the distal-most clip of the plurality of clips into the end effector when the tab assembly is advanced distally to a second position.

\* \* \* \* \*